(12) United States Patent
Jung et al.

(10) Patent No.: US 9,200,315 B2
(45) Date of Patent: Dec. 1, 2015

(54) REAGENT CONTAINER FOR AMPLIFYING NUCLEIC ACID, METHOD OF PREPARING THE REAGENT CONTAINER, METHOD OF STORING THE REAGENT, AND MICROFLUIDIC SYSTEM FOR NUCLEIC ACID ANALYSIS

(71) Applicant: Samsung Electronics Co. Ltd., Suwon-si, Gyeonggi-do (KR)

(72) Inventors: Sung-ouk Jung, Hwaseong-si (KR); Sung-min Chi, Hwaseong-si (KR); Soo-kwan Lee, Seoul (KR); Sung-hong Kwon, Yongin-si (KR); Joon-ho Kim, Seongnam-si (KR); Kak Namkoong, Seoul (KR); Chin-sung Park, Yongin-si (KR); Kyu-youn Hwang, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/095,784

(22) Filed: Dec. 3, 2013

(65) Prior Publication Data
US 2014/0154688 A1   Jun. 5, 2014

(30) Foreign Application Priority Data

Dec. 3, 2012  (KR) .......................... 10-2012-0139266
Mar. 20, 2013  (KR) .......................... 10-2013-0029921

(51) Int. Cl.
*C12Q 1/68* (2006.01)
*B01L 3/00* (2006.01)
*B01L 7/00* (2006.01)

(52) U.S. Cl.
CPC ............ *C12Q 1/6806* (2013.01); *B01L 3/5027* (2013.01); *B01L 3/527* (2013.01); *B01L 3/502707* (2013.01); *B01L 7/52* (2013.01); *B01L 2200/04* (2013.01); *B01L 2200/0684* (2013.01); *B01L 2200/10* (2013.01); *B01L 2200/141* (2013.01); *B01L 2200/16* (2013.01); *B01L 2300/0816* (2013.01); *B01L 2300/0861* (2013.01); *B01L 2300/0864* (2013.01);
(Continued)

(58) Field of Classification Search
None
See application file for complete search history.

(56) References Cited

U.S. PATENT DOCUMENTS 5,413,732 A   5/1995  Buhl et al.
5,624,597 A   4/1997  Buhl et al.
(Continued)

FOREIGN PATENT DOCUMENTS

EP   2202302 A1   6/2010
EP   2460589 A1   6/2012
(Continued)

OTHER PUBLICATIONS

Boscaini et al, "Investigation of fundamental physical properties of a polydimethylsiloxane (PDMS) membrane using a proton transfer reaction mass spectrometer (PTRMS)," *International Journal of Mass Spectrometry*, 239: 179-186 (2004).
(Continued)

Primary Examiner — Samuel Woolwine
(74) Attorney, Agent, or Firm — Leydig, Voit & Mayer, Ltd.

(57) ABSTRACT

Provided is a reagent container that can maintain stability of a reagent for a long period of time, a method of preparing the reagent container, a method of storing the reagent, and microfluidic systems for conducting cell binding, lysis, nucleic acid extraction, and amplification.

19 Claims, 32 Drawing Sheets

(52) U.S. Cl.
CPC .. *B01L2300/0867* (2013.01); *B01L 2400/0487* (2013.01)

(56) References Cited

U.S. PATENT DOCUMENTS

| | | | |
|---|---|---|---|
| 5,776,563 | A | 7/1998 | Buhl et al. |
| 5,998,031 | A | 12/1999 | Buhl et al. |
| 6,077,669 | A * | 6/2000 | Little et al. .......................... 435/5 |
| 6,103,465 | A * | 8/2000 | Johnston-Dow et al. .... 435/6.12 |
| 6,251,684 | B1 | 6/2001 | Buhl et al. |
| 7,972,838 | B2 | 7/2011 | Korpimaki et al. |
| 2001/0055812 | A1* | 12/2001 | Mian et al. ...................... 436/45 |
| 2004/0161788 | A1 | 8/2004 | Chen et al. |
| 2005/0089863 | A1* | 4/2005 | Karlsen et al. .................... 435/6 |
| 2007/0243601 | A1 | 10/2007 | Korpimaki et al. |
| 2010/0055766 | A1* | 3/2010 | Hwang et al. ................ 435/259 |
| 2010/0209973 | A1 | 8/2010 | Kim et al. |
| 2011/0014606 | A1* | 1/2011 | Steinmetzer et al. ............. 435/6 |
| 2012/0142070 | A1 | 6/2012 | Battrell et al. |

FOREIGN PATENT DOCUMENTS

| | | | |
|---|---|---|---|
| KR | 10-2006-0081575 | A | 7/2006 |
| KR | 10-2008-0118749 | A | 11/2009 |
| WO | WO 98/07019 | A1 | 2/1998 |
| WO | WO 03/060157 | A2 | 7/2003 |
| WO | WO 2007/106579 | A2 | 9/2007 |
| WO | PCT/GB2008/002036 | A1 | 12/2008 |
| WO | WO 2008/155529 | A1 | 12/2008 |

OTHER PUBLICATIONS

Boxshall, "Simple surface treatments to modify protein adsorption and cell attachment properties within a poly (dimethylsiloxane) micro-bioreactor," *Surface and Interface Analysis*, 38: 198-201 (2006).

European Patent Office, Extended Search Report in Application No. 13195307.7, dated Apr. 15, 2015, pp. 1-9.

* cited by examiner

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Synthetic ([3a]mecA-99 forward primer)

<400> SEQUENCE: 1
attaacccag tacagatcct ttcaatc                27

<210> SEQ ID NO 2
<211> LENGTH: 25
<212> TYPE: DNA
<213> ORGANISM: Artificial Sequence
<220> FEATURE:

```
<223> OTHER INFORMATION: Synthetic ([3a]mecA-99 reverse primer)

<400> SEQUENCE: 2
ccaaactttg tttttcgtgt ctttt                                              25

<210> SEQ ID NO 3
<211> LENGTH: 20
<212> TYPE: DNA
<213> ORGANISM: Artificial Sequence
<220> FEATURE:
<223> OTHER INFORMATION: Synthetic ([3a]mecA-99 probe)

<400> SEQUENCE: 3
tattaacgca cctcacttat                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic (SA442_76 forward primer)

<400> SEQUENCE: 4
cgttgcatcg gaaacattgt                                                    20

<210> SEQ ID NO 5
<211> LENGTH: 27
<212> TYPE: DNA
<213> ORGANISM: Artificial Sequence
<220> FEATURE:
<223> OTHER INFORMATION: Synthetic (SA442_76 reverse primer)

<400> SEQUENCE: 5
atgaccagct tcggtactac taaagat                                            27

<210> SEQ ID NO 6
<211> LENGTH: 18
<212> TYPE: DNA
<213> ORGANISM: Artificial Sequence
<220> FEATURE:
<223> OTHER INFORMATION: Synthetic (SA442_76 Probe)

<400> SEQUENCE: 6
ttctgtatgt aaaagccg                                                      18
```

REAGENT CONTAINER FOR AMPLIFYING NUCLEIC ACID, METHOD OF PREPARING THE REAGENT CONTAINER, METHOD OF STORING THE REAGENT, AND MICROFLUIDIC SYSTEM FOR NUCLEIC ACID ANALYSIS

CROSS-REFERENCE TO RELATED APPLICATIONS

This application claims the benefit of Korean Patent Application No. 10-2012-0139266, filed on Dec. 3, 2012, and Korean Patent Application No. 10-2013-0029921, filed on Mar. 20, 2013 in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,665 Byte ASCII (Text) file named "715536_ST25Updated.txt" created on Feb. 13, 2014.

BACKGROUND

1. Field

The present disclosure relates to reagent containers for amplifying nucleic acids, methods of preparing the reagent containers, methods of storing reagents, and microfluidic systems for conducting cell binding, lysis, nucleic acid extraction, and amplification.

2. Description of the Related Art

Polymerase chain reaction (PCR) is a method of amplifying a specific target genetic material to be detected, which is used in many assays of genetic material. A large amount of identical genetic copies may be produced from a small starting amount by PCR, allowing genetic material to be used to diagnose various kinds of genetic and infectious diseases and for other purposes. PCR may be applied to any genetic materials, including human bacteria, viruses, or fungi genetic material.

In addition, due to the safety, convenience, and immediate point of care testing (POCT) required for users, a diagnostic device has been gradually miniaturized and automated. Such a miniaturized and automated diagnostic device uses a solid reagent (i.e., a lyophilized reagent) rather than a liquid reagent because the liquid reagent is difficult to store and is less reliable due to its decreased stability in comparison to the solid reagent. The solid reagent is safer due to a higher shelf life, and may allow for a reduced product size due to the small volume of the reagent required to be stored in the container.

Nevertheless, new methods and devices are needed for more efficiently or effectively storing and using PCR reagents.

SUMMARY

Provided is a kit useful for amplifying nucleic acids, the kit comprising a reagent container comprising a first well and a second well, wherein the first well contains a first reagent comprising a nucleotide, a nucleic acid component, an enzyme, or a combination thereof without a reaction buffer; and the second well contains a second reagent comprising a reaction buffer for amplifying a nucleic acid.

Also provided is a reagent container useful for containing reagents for amplifying nucleic acids. The reagent container comprises a first well; a second well; a connection part connecting the first and second wells, wherein the connection part is a groove, channel, partition, or film; a first aperture in the first well leading out of the reagent container; and a second aperture in the second well leading out of the reagent container.

A microfluidic system is provided that comprises the reagent container or kit. In some embodiments, the system is capable of conducting a series of processes of capturing cells in a sample, extracting nucleic acid by lysis of the captured cells, and performing a nucleic acid amplification reaction in a single device. Further provided is a method of storing reagents for amplifying nucleic acids by disposing a first reagent comprising a nucleotide or nucleic acid into a first well of a reagent container, wherein the first well of the reagent container does not contain a reaction buffer; disposing a second reagent comprising a reaction buffer into a second well of a reagent container; and solidifying the first reagent by drying; wherein the wherein the first and the second reagent are for amplifying nucleic acids.

BRIEF DESCRIPTION OF THE DRAWINGS

These and/or other aspects will become apparent and more readily appreciated from the following description of the embodiments taken in conjunction with the accompanying drawings, in which.

DETAILED DESCRIPTION

Figure 1:
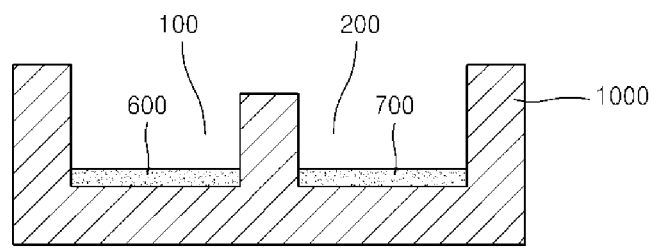
FIG. 1 is a front view illustrating a reagent container.

Additional aspects of the invention will be set forth in part in the description which follows and, in part, will be apparent from the description, or may be learned by practice of the presented embodiments. As used herein, the term "and/or" includes any and all combinations of one or more of the associated listed items. Expressions such as "at least one of," when preceding a list of elements, modify the entire list of elements and do not modify the individual elements of the list.

According to an aspect of the present inventive concept, a reagent container includes a first well that stores a first reagent having a nucleotide or nucleic acid component free of reaction buffer, and a second well that stores a second reagent having a reaction buffer, wherein the first and second reagents are for amplifying a nucleic acid.

With regard to the reagent container, the nucleotide or nucleic acid component may include nucleotide, deoxynucleotide, or ribonucleotide triphosphate; and a primer; and optionally a probe. The first reagent may further include an enzyme.

A shape of sectional views of the first and/or second well may vary. The shape may be circular, double-circular, oval, or polygonal such as in the case of a rectangle or a pentagon. A size of the first and/or second well may be in a range of microliters. For example, a size of the well is in a range of about 1 to about 10 ul, e.g., in a range of about 1 to about 9 ul, about 1 to about 8 ul, about 1 to about 7 ul, about 1 to about 6 ul, about 1 to about 5 ul, about 1 to about 4 ul, about 1 to about 3 ul, or about 1 to about 2 ul in volume.

The reagent container may further include a first aperture connected with the first well and a second aperture connected with the second well. The first aperture may be connected in fluid communication with the first well. The second aperture may be connected in fluid communication with the second well. The first and second apertures provide a passage from the wells to the exterior of the reagent container, and may serve as an entry and/or an exit of the reagent container. The first and second apertures may be placed in the upper part (e.g., the "top") of the reagent container. In addition, an upper part of the first and/or second aperture may be open. In other words, the apertures may be provided by grooves that extend along the top of the reagent container from an outer edge of the container to the interior of the well.

The reagent container may be implemented (e.g. installed) on a rehydration chamber. The reagent container may be the rehydration cover when the reagent container is implemented on a rehydration chamber, which covers or encloses a rehydration chamber.

The first and second apertures may be implemented to be connected with the rehydration chamber and in fluid communication therewith. The reagent container is to be installed upside down and on the rehydration chamber, such that the open upper part of the apertures (open sides of the grooves providing the apertures) contacts an outer surface of the rehydration chamber, thereby forming a channel (an enclosed channel). The rehydration chamber may be used in a device or microfluidic system for nucleic acid analysis. The nucleic acid analysis may include a PCR.

The reagent container may further include a connection part connecting the first well to the second well. The connection part may be a groove, a channel, a partition, or a film. The groove may have an open upper part. The channel may further include a valve therein, also the valve may be opened and closed. The openable and closable valve may be appropriately chosen by those of ordinary skill in the art. The partition may be defined by a common sidewall in contact with the first and second wells, and a height of the partition may be shorter than that of the first and second wells. The film may be friable. The film may be easily destroyed due to the pressure of the fluid to be injected into the reagent container. The film may also be porous.

The reagent container may comprise a plurality of protrusions formed on a substantially flat substrate, wherein the first well and the second well may be provided by two subgrooves separated from each other and recessed in a predetermined shape on the plurality of protrusions. A side of the first well and the second well may have a curved shape and with the smallest width at a center portion thereof. In other words, when viewed from the "top" looking into the wells, the wells have a curved shape comprising two curved side portions that meet at the center of the well, wherein the center of the well is narrower than the sides of the well. An external angle θ formed by corners of both sides of the subgroove at a position having the narrowest width is in a range of about 30 degrees to about 90 degrees.

With regard to the reagent container, the reagent for amplifying the nucleic acids may be a PCR premix.

The term "primer" used in the present specification refers to a single-stranded oligonucleotide that may serve as a starting point for a template-dependent DNA synthesis under suitable temperature and conditions in suitable buffers, e.g., 4 different nucleosides, nucleotides, deoxynucleotides, or ribonucleotide triphosphates; and polymerase such as DNA polymerase, RNA polymerase or reverse transcriptase. Appropriate length of the primer may vary depending on the purpose of its intended use and may be in a range of about 15 to about 30 nucleotides. A primer sequence does not have to be fully complementary to a template but has to be complementary enough to hybridize with a template. Such primer is used in pairs with a second primer that is able to hybridize on the opposite side.

The term "probe" used in the present specification refers to a polynucleotide that may specifically bind to a specific target nucleic acid to confirm a presence of the target nucleic acids. The probe may be a single-stranded nucleic acid. The "target nucleic acid" refers to a nucleic acid to be analyzed. The nucleic acid may have a sequence complementary to the probe nucleic acid. The target nucleic acid includes a sequence complementary to the probe nucleic acid, and when the target nucleic acid is hybridized with the probe nucleic acid, the hybridized sequence may have mismatch of about 0 to about 5 bp therein. The probe nucleic acid may be labeled by a detectable label, and examples of the detectable label are already known. For example, the label may be selected from a group consisting of a label generating light signal, a radioactive label, and a label generating electrical signal. For example, the label may be a fluorescent substance generating fluorescence signal. Examples of the fluorescence substances are Cal610, fluorescein, rhodamine, cyanines including Cy3 or Cy5, and a complex of metal porphyrin. Examples of fluorescein dye are 6-carboxylfluorescein (6-FAM) 1,2',4',1, 4,-tetrachlorofluorescein (TET) and 2',4',5',7',1,4-hexachlorofluorescein (HEX), 2',7'-dimethoxy-4',5'-dichloro-6-carboxylrhodamine (JOE), 2'-chloro-5'-fluoro-7',8'-fused phenyl-1,4-dichloro-6-carboxylfluoresein, and 2'-chloro-7'-phenyl-1,4-dichloro-6-carboxylfluoresein. A substance of the detectable signal may be attached to atoms of bases of the probe nucleic acid.

Enzymes used herein may be known to those of ordinary skill in the art. The enzyme may be selected from a group consisting of a DNA polymerase, a reverse transcriptase, a RNA polymerase, a RNAase H, and a combination thereof. The DNA polymerase may be used in a PCR. The DNA polymerase may be thermally stable. The DNA polymerase may be separated from thermophiles. Also, the DNA polymerase may be separated from *Thermus aquaticus* or *Thermococcus litoralis*.

The nucleotide, deoxynucleotide, or ribonucleotide triphosphate may be NTP, dNTP or rNTP, respectively. The NTP refers to ATP, CTP, GTP, and TTP of the nucleotide triphosphate. The dNTP refers to dATP, dCTP, dGTP, and dTTP of the deoxynucleotide triphosphate. The rNTP refers to rATP, rCTP, rGTP, and rTTP of the ribonucleotide triphosphate. The nucleotide, deoxynucleotide, or ribonucleotide triphosphate may be or may not be labeled with a detectable label. Examples of the detectable labels are the same as described above.

The first reagent may further include a stabilizer, which may be an enzyme stabilizer. The enzyme stabilizer may assist an enzyme to maintain its activity. The enzyme stabilizer may be selected from a group consisting of glycerol, glucose, sucrose, fructose, sorbitol, trehalose, raffinose, melezitose, and a combination thereof. The stabilizer may stabilize the activity of the enzymes. The stabilizer may be lyophilized in a state of being more concentrated than the concentration used in a reaction.

The term "buffer" as used herein refers to an agent including free ions capable of preventing changes in the pH of a solution, which includes a mixture of a weak acid and its conjugate base or a weak base and its conjugate acid. The buffer provides a buffer condition for the polymerase activity. The buffer may be appropriately used by those of ordinary skill in the art. For example, the buffer may be a commercially available polymerase buffer depending on the selected polymerase. For example, the buffer may be a Taq polymerase buffer. Such buffer may provide a buffer condition for a polymerase activity and a ligase activity at the same time. The buffer condition for the polymerase is deemed to be compatible with the condition for the ligase in general. Examples of the buffer are $MgCl_2$, $Na_2HPO_4$, $NaH_2PO_4$, MOPS-KOH, HEPES-NaOH, tris(hydroxymethyl)aminomethan-HCl, borate, or glycin-NaOH. The buffer may be lyophilized in a state of being more concentrated than the concentration used in the reaction.

The first and second solid reagents may further include an additive. The additive may be an anti-foaming agent or a surfactant. The anti-foaming agent or surfactant may be appropriately selected by those of ordinary skilled in the art. The first and second reagents may further include other components needed for the reaction such as water, a substrate, a cofactor, or a coenzyme. The water may be sterile distilled water.

The first reagent may be a solid reagent. The second reagent may be a solid reagent. The first and/or second reagent may be a dried reagent. The drying may include a natural drying, a lyophilization, or a vacuum drying. The drying may be appropriately selected by those of ordinary skill in the art. Also, the second reagent may be a liquid reagent. The reagent container may be for storing the reagent. The enzyme; nucleotide, deoxynucleotide, or ribonucleotide triphosphate; primer; probe; buffer; stabilizer; or additive may be lyophilized in a state of being more concentrated than the concentration used in a reaction. The buffer may be lyophilized in a state of being more concentrated by about 1.5 to about 2.5-fold, about 1.6 to about 2.4-fold, about 1.7 to about 2.3-fold, about 1.8 to about 2.2-fold, or about 1.9 to about 2.1-fold than the concentration used in a reaction.

The reagent container may be easily modified in shape, and the surface thereof may be made of biologically inactive substances. The reagent container may be made of a material having a chemical or biological stability. The reagent container may be made of a material having machinability. The reagent container may be formed of optically transparent materials. The reagent container may be made of polymer materials. The polymer materials may be selected from a group consisting of polypropylene, polyethylene, polystyrene, polymethyl methacrylate, polyolefin, and a combination thereof. The polymer material may be an oxygen containing polymer. The oxygen may be any oxygen of siloxane, carbonyl, ester, or ether. The polymer material may include a polysiloxane. Examples of the polymer materials are polydimethylsiloxane (PDMS), polymethylphenylsiloxane (PMPS), polydimethyldiphenylsiloxane, or polyvinylsiloxane (PVS). The polymer material may be a silicon polymer including alkylsiloxane or organosiloxane, which are generally described as polysiloxane, The reagent container may further include a plurality of wells. The plurality of wells may be arranged in a direction of an X axis or a Y-axis, an array, or in a different direction. Each of the plurality of wells may separately store a reagent belonging to the first reagent, the reagent of which activity is declined when the reagents are mixed and dried.

According to another aspect of the present inventive concept, a microfluidic system includes a rehydration chamber, the reagent container that is implemented on the rehydration chamber, an amplification chamber, and a flow channel system forming an integrated fluid flow between the rehydration chamber and the amplification chamber. In the rehydration chamber, a cell lysate and a nucleic acid amplification reagent disposed in the container are mixed to form an amplification reaction mixture, whereas in the amplification chamber, a nucleic acid amplification reaction is performed on the amplification reaction mixture introduced from the rehydration chambers.

The system may include a plurality of rehydration chambers, and each of the plurality of rehydration chambers may include two separated subchambers, and the nucleic acid amplification reagent may be divided and disposed in the two subchambers. The two subchambers correspond to the rehydration cover, i.e., the first well and the second well of the reagent container, and may be able to accept each of the first well and the second well, because the reagent container may be installed upside down and on the rehydration chamber.

The nucleic acid amplification reagent may be disposed in each of the plurality of rehydration chambers.

A side of the subchamber may have a curved shape, and a width of a flow path of the introduced cell lysate may be the smallest at a center portion thereof.

A plurality of second through holes forming spaces of the plurality of rehydration chambers are formed. With regard to the reagent container, which is the rehydration cover covering the plurality of second through holes, a plurality of protrusions may be formed at positions corresponding to the plurality of second through holes, and a plurality of grooves recessed in a predetermined shape may be formed on the plurality of protrusions.

A diameter of the protrusion may be formed to be larger than a diameter of the second through hole, and sealing of the groove may be performed by inserting the protrusion into the second through hole.

In the rehydration cover covering the plurality of second through holes, a plurality of grooves recessed in a predetermined shape are formed at positions corresponding to the plurality of second through holes, and the rehydration cover may be provided, wherein the nucleic acid amplification reagent that is in a freeze-dried state is disposed in the grooves.

Each of the plurality of grooves includes two subgrooves separated from each other, and the nucleic acid amplification reagent may be divided and disposed in the two subgrooves. The two subgrooves may be the first well and the second well of the reagent container.

The nucleic acid amplification reagent may be disposed in the first well and the second well in each of the plurality of grooves. The nucleic acid amplification reagent disposed in the first well and the second well is the same as described above.

A side of the subgroove has a curved shape and has a smallest width at a center portion thereof.

An external angle formed by corners of both sides of the subgroove at a position having the narrowest width is in a range of about 30 degrees to about 90 degrees.

The microfluidic system for analyzing nucleic acid includes: a reagent supply device including a sample chamber in which a sample as an examination target is injected, a plurality of reagent chambers in which a reagent for extracting nucleic acid from the sample is injected, and a waste chamber in which the used reagent is discarded; a binding-lysis chamber in which cells are captured from the sample, the captured cells are lysed to form a cell lysate containing nucleic acid, and a plurality of particles for cell binding are disposed; a plurality of rehydration chambers in which the cell lysate and the nucleic acid amplification reagent disposed in the container are mixed to form an amplification reaction mixture; a reagent container that is implemented on the rehydration chamber; a plurality of amplification chambers in which a nucleic acid amplification reaction is performed on the amplification reaction mixture introduced from the plurality of rehydration chambers; and a flow channel system including an outlet and a plurality of inlets connected to the reagent supply device and forming an integrated fluid flow between the binding-lysis chamber, the rehydration chambers, and the amplification chambers. The cell lysate may be formed in the binding-lysis chamber, and distributed and introduced to the plurality of rehydration chambers.

The one or more reagent chambers may include a lysis buffer chamber in which a lysis buffer is injected and a washing buffer chamber in which a washing buffer is injected.

A destruction pattern may be formed on each bottom surface of the sample chamber, the lysis buffer chamber, and the washing buffer chamber. The destruction chamber is breachable or rupturable by an external impact to discharge an injected solution from the chamber. The plurality of inlets of the flow channel system may have the shape of a needle for breaching or rupturing the destruction pattern.

The destruction pattern may also be formed on a bottom surface of the waste chamber, and the outlet of the flow channel system may have the shape of a needle for breaching or rupturing the destruction pattern.

The microfluidic system for analyzing nucleic acid may further include one or more metering chambers for quantifying an amount of reagent from one or more of the reagent chambers (e.g., the lysis buffer supplied from the lysis buffer chamber and/or washing buffer from the washing buffer chamber) of the reagent supply device.

The microfluidic system for analyzing nucleic acid may further include one or more bubble trap chambers for removing bubbles generated in the binding-lysis chamber during cell lysis.

The diameters of the particles prepared in the binding-lysis chamber may be in the range of about 1 μm to about 1000 μm, and an amount of the particle may be in the range of about 1 mg to about 100 mg.

The microfluidic system for analyzing a nucleic acid may further include a plurality of metering chambers for quantifying an amount of the cell lysate formed in the binding-lysis chamber and for distributing the cell lysate into the plurality of rehydration chambers.

The microfluidic system for analyzing nucleic acid may include: a fluid flow part in which the inlets and the outlet connected to the reagent supply device are formed on a top surface thereof, the fluid flow part including a first through hole forming a ports to the binding-lysis chamber and a plurality of second through holes forming ports to the plurality of rehydration chambers are formed, and a recessed groove pattern on a bottom surface thereof for forming spaces of the plurality of nucleic acid amplification chambers; a membrane part bonded to the bottom surface of the fluid flow part to form bottom surfaces of the binding-lysis chamber and of the plurality of rehydration chambers, the membrane part formed of an elastic material; and a pneumatic part bonded to a bottom surface of the membrane part, the pneumatic part having a plurality of ports for applying pneumatic pressure at a predetermined position of the membrane part formed in the pneumatic part.

A microchannel for implementing the flow channel system and a microvalve for preventing flow of a fluid passing along the microchannel by pneumatic pressure applied from the pneumatic part may be formed on the bottom surface of the fluid flow part.

A plurality of particles for cell binding may be disposed in the first through hole of the fluid flow part and a particle cover covering the first through hole may be included.

The microfluidic system for analyzing nucleic acid may further include a rehydration cover covering the plurality of second through holes of the fluid flow part, wherein a plurality of protrusions is formed at positions corresponding to the plurality of second through holes, a plurality of grooves recessed in a predetermined shape is formed on the plurality of protrusions, and the nucleic acid amplification reagent in a freeze-dried state is disposed in the grooves.

The diameters of the protrusions may be formed to be larger than the diameters of the second through holes, and sealing of the groove may be performed by inserting the protrusions into the second through holes.

The microfluidic system for analyzing nucleic acid may further include a rehydration cover covering the plurality of second through holes, wherein a plurality of grooves recessed in a predetermined shape are formed at positions corresponding to the plurality of second through holes, and the nucleic acid amplification reagent is in a freeze-dried state.

The microfluidic system for analyzing nucleic acid may further include a PCR film forming a bottom surface of the nucleic acid amplification chamber and covering the groove pattern recessively formed on the bottom surface of the fluid flow part.

A bridge pattern having a shape recessed from the top surface of the fluid flow part may be formed on the top surface of the fluid flow part, the shape forming a path in which the amplification reaction mixture formed in the rehydration chamber is transferred to the nucleic acid amplification chamber.

The bridge pattern may include a plurality of subpatterns, and each of the plurality of subpatterns may be formed by including a hole penetrating the fluid flow part to face the membrane part, a hole penetrating the fluid flow part to face the PCR film, and a recessed bridge groove connecting the two holes on the top surface of the fluid flow part.

A bridge cover entirely covering the plurality of subpatterns may be prepared on the top surface of the fluid flow part.

The microfluidic system for analyzing nucleic acid may further include a recess pattern on the bottom surface of the fluid flow part for forming one or more metering chambers for quantifying an amount of the lysis buffer supplied from the lysis buffer chamber of the reagent supply device.

The microfluidic system for analyzing nucleic acid may further include on the bottom surface of the fluid flow part a recess pattern for forming one or more bubble trap chambers for removing bubbles generated in the binding-lysis chamber during cell lysis.

A recess pattern for forming a plurality of metering chambers for quantifying an amount of the cell lysate formed in the binding-lysis chamber and distributing the cell lysate into the plurality of rehydration chambers may be formed on the bottom surface of the fluid flow part.

A guide part for installing the reagent supply device may be further disposed on an upper portion of the fluid flow part.

The fluid flow part may be formed of a transparent polymer material, such as, any one of polycarbonate (PC), polymethyl methacrylate (PMMA), polystyrene (PS), cyclic olefin copolymer (COC), polydimethylsiloxane (PDMS), and silicone.

The membrane part may be formed of polydimethylsiloxane (PDMS) or silicon.

The pneumatic part may be formed of a transparent polymer material.

According to another aspect of the present inventive concept, a method of manufacturing a reagent container includes preparing a first reagent by mixing an enzyme; nucleotide, deoxynucleotide, or ribonucleotide triphosphate; and a primer; and optionally a probe, disposing a first reagent in a first well of a reagent container, disposing a second reagent in a second well of a reagent container, and drying and solidifying the first reagent, wherein the second reagent includes a buffer.

According to another aspect of the present inventive concept, a method of storing a reagent includes preparing a first reagent by mixing an enzyme, nucleotide, deoxynucleotide, ribonucleotide triphosphate, or a primer, disposing a first reagent in a first well of a reagent container, disposing a second reagent into a second well of the reagent container, wherein the second reagent includes a buffer, and solidifying the first reagent by drying. The reagent container includes a first well having a first reagent including a nucleotide or nucleic acid component and a second well having a second reagent including a buffer, wherein the first and second reagent are for amplifying nucleic acids. The reagents for amplifying the nucleic acids may be a PCR premix. The first reagent may further include a probe.

The enzyme; nucleotide, deoxynucleotide, or ribonucleotide triphosphate; primer; probe; stabilizer; and additive are the same as described above. In the preparing a first reagent by mixing an enzyme; nucleotide, deoxynucleotide, or ribonucleotide triphosphate; and a primer, the first reagent may further include a probe or a stabilizer. The enzyme, nucleotide, deoxynucleotide, ribonucleotide triphosphate, primer, probe, stabilizer, or additive may be a liquid. The buffer may be dried and solidified. The first and/or second reagent may further include an additive. The drying may be at least one selected from a lyophilization and a natural drying. The buffer may be lyophilized in a state of being more concentrated than a concentration used in a reaction. The reagent container is the same as described above.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a front view illustrating a reagent container according to an embodiment of the present inventive concept. As illustrated by FIG. 1, a reagent container 1000 includes a first well 100 storing a first reagent 600 and a second well 200 storing a second reagent 700. The first reagent 600 may be an enzyme; nucleotide, deoxynucleotide, or ribonucleotide triphosphate; and a primer; and optionally a probe. The first reagent 600 may optionally include a stabilizer of the enzyme or an additive. The first reagent does not comprise a reaction buffer. The second reagent 700 may include a buffer and optionally include an additive. The first and second reagents 600 and 700 may be used for PCR premix.

After the first reagent 600 has been prepared, it may be disposed in the first well 100 of the reagent container 1000. The second reagent 700 may be disposed in the second well 200 of the reagent container 1000. The first reagent 600 may be dried and thus solidified, and the second reagent 700 may be optionally dried and thus solidified. The reagent container 1000 may be manufactured by a method as described above. In addition, the first and/or second reagent 700 and/or 800 may be stored in the reagent container 1000.

Figure 2:
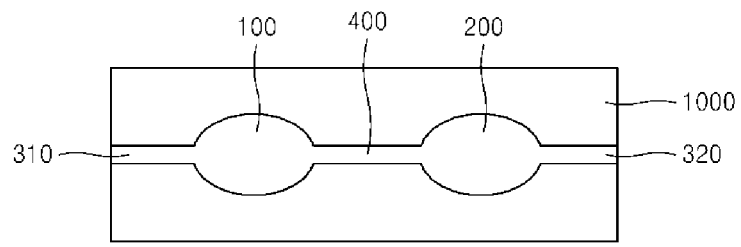
FIG. 2 is a plan view illustrating a reagent container.

FIG. 2 is a plan view illustrating a reagent container according to an embodiment of the present inventive concept. As illustrated by FIG. 2, the reagent container 1000 may include a connection part 400 connecting the first well 100 with the second well 200. The connection part may link the wells by a channel or groove that is fluidly connected to both wells, or the connection part may be a separation wall or breachable film that divides the wells. The reagent container 1000 may include a first aperture 310 connected with the first well 100 and a second aperture 320 connected with the second well 200. The first and second apertures 310 and 320 may serve as an entry and/or exit of the reagent container 1000. The first and second apertures 310 and 320 may be formed inside the walls of the wells, or on upper part (e.g., upper surface) of the reagent container 1000. The apertures formed inside the container may form a channel connected in fluid communication with the wells. The apertures formed on upper part of the container may form a groove connected in fluid communication with the wells. Through the first and/or second apertures 310 and 320, a reagent including a target nucleic acid may be injected, and a mixture of the reagent including the target nucleic acid and the first and second reagents may be released therethrough.

Figure 3:
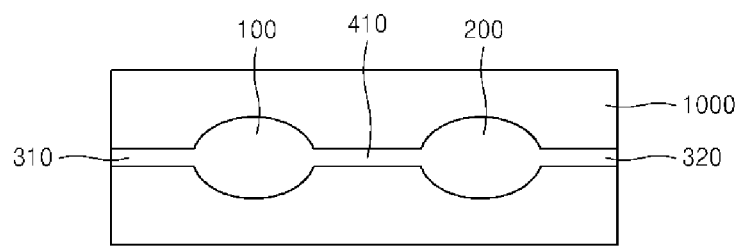
FIGS. 3 through 6 are plan views illustrating a reagent container including one example of a connection part.
Figure 4:
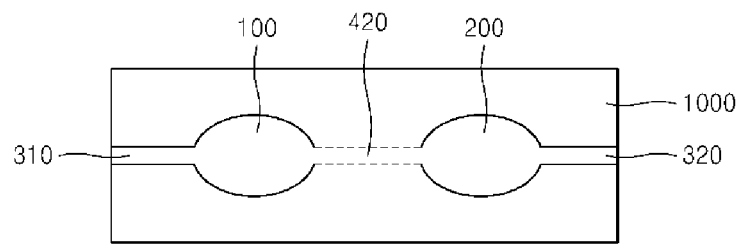

FIGS. 3 through 4 are plan views each illustrating a reagent container including an exemplary connection part according to an embodiment of the present inventive concept.

As illustrated by FIG. 3, the reagent container 1000 may include a groove 410 connecting the first well 100 and the second well 200 to each other. An upper part of the groove 410 may be opened.

As illustrated by FIG. 4, the reagent container 1000 may include a channel 420 connecting the first well 100 and the second well 200 to each other. The channel 420 may further include a valve therein (not shown). The valve may be opened and/or closed. The valve may be appropriately selected by those of ordinary skilled in the art.

Figure 5:
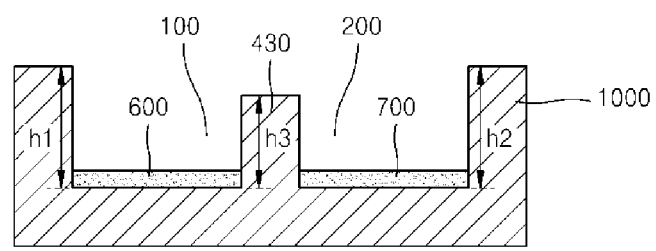
Figure 6:
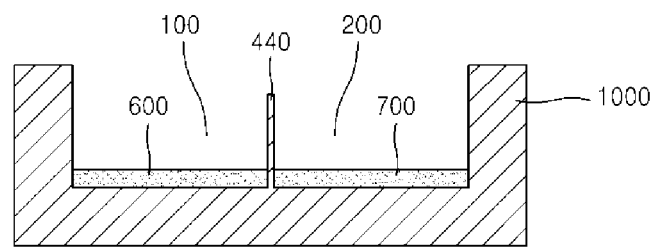

FIGS. 5 and 6 are front views illustrating a reagent container including one exemplary of a connection part according to an embodiment of the present inventive concept.

As illustrated by FIG. 5, the reagent container 1000 may include a partition 430 physically connecting the first well 100 and the second well 200 to each other. The partition 430 may be defined as a common sidewall in contact with the first well 100 and the second well 200. A height h3 of the partition 430 may be lower than or the same as that of the first and second wells h1 and h2. The low height h3 of the partition 430 allows reagents that are taken in the first and the second wells 100 and 200 to come in contact with each other, e.g., to mix with each other upon rehydration.

As illustrated by FIG. 6, the reagent container 1000 may include a film 440 connecting the first well 100 and the second well 200 to each other. The film 440 is a common sidewall in contact with the first well 100 and the second well 200 and may be easily destroyed. The film 440 may be a friable film. The film 440 may be easily destroyed by the pressure of the fluid to be injected. When the film 440 is destroyed, the reagents stored in the first and second wells 100 and 200 may come into contact with, e.g., mix with each other. Also, the film 440 may be porous allowing the dissolved reagents to pass therethrough. The first and second reagents 600 and 700 may be dissolved by a fluid to be injected into the reagent container 1000 later and the reagents may pass through the porous film.

Figure 7:
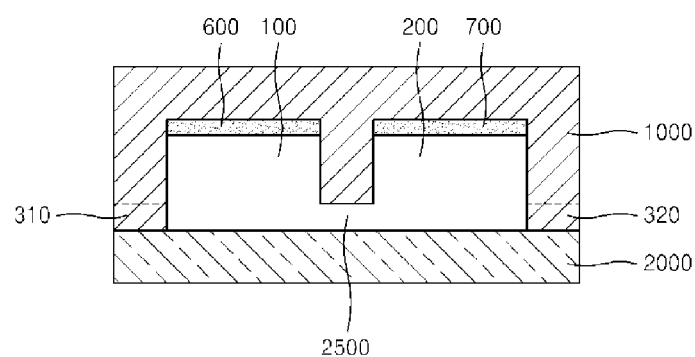
FIG. 7 is a front view illustrating a reagent container installed on a rehydration chamber.

FIG. 7 is a front view illustrating a reagent container 1000 installed on a rehydration chamber 2000 according to an embodiment of the present inventive concept. As illustrated by FIG. 7, when the reagent container 1000 is installed on one side of the rehydration chamber 2000, the first and second apertures 310 and 320 may be connected to a channel (not shown) of the rehydration chamber 2000 in fluid communication, and thus a reagent including a target nucleic acid may be injected into the reagent container 1000 through the rehydration chamber 2000. The installation includes the reagent container 1000 placed upside down and on the rehydration chamber 2000, and the first and second apertures 310 and 320 each having an open top may be in contact with an outer side of the rehydration chamber 2000 and thus form one channel 2500. The channel 2500 may be surrounded by the first well 100, the second well 200, the connection part 400 of the reagent container 1000, and the outer side of the rehydration chamber 2000. The entry and/or exit of the channel may be formed by the first and/or second aperture, and the outer surface of the rehydration chamber 2000. The rehydration chamber may be one used in a PCR apparatus. The PCR apparatus may include a chamber (not shown) where PCR occurs. The mixture of the reagent including a target nucleic acid, and the first and second reagents, may be discharged and introduced into the chamber.

Figure 12:
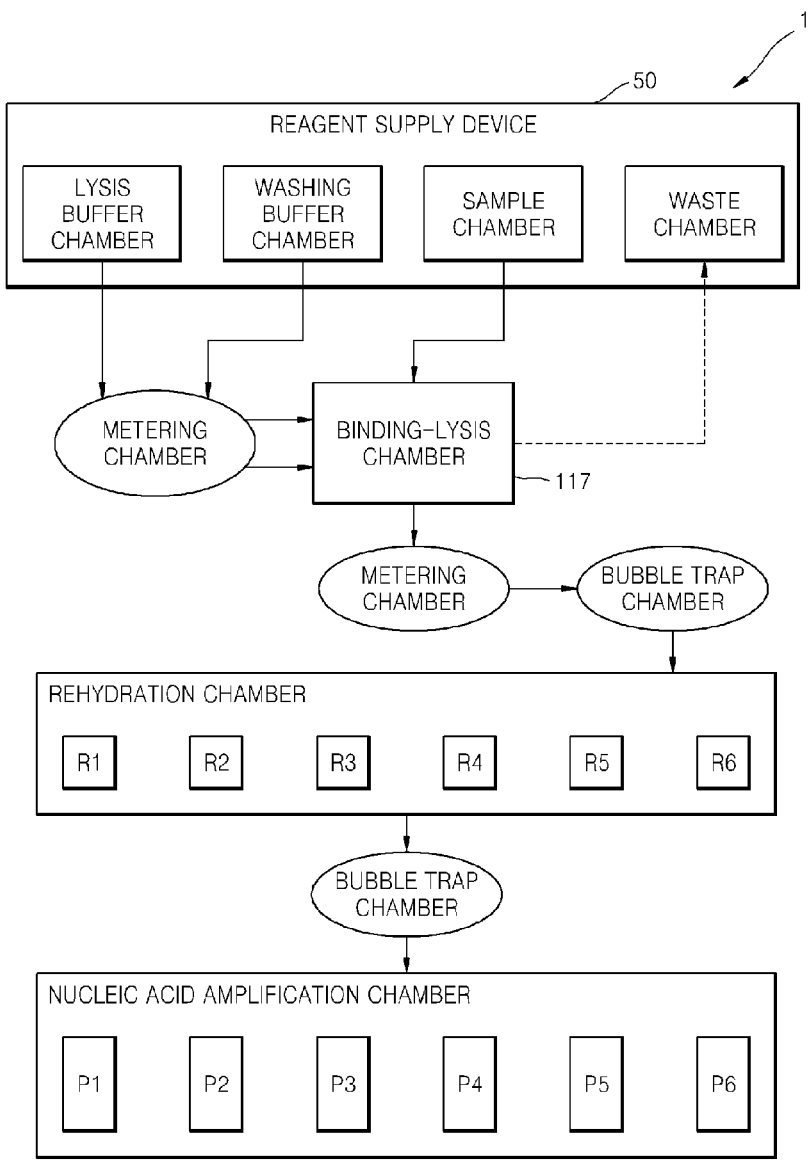
FIG. 12 is a block diagram illustrating a schematic structure of a microfluidic system.
Figure 13:
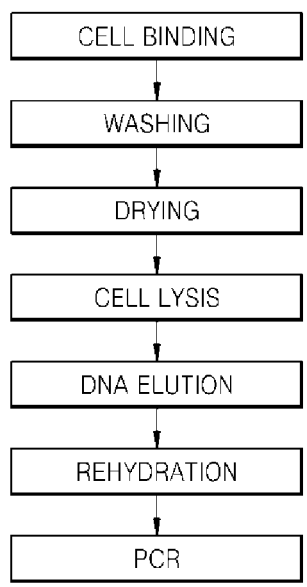
FIG. 13 is a flowchart illustrating a series of processes performed in the microfluidic system.

FIG. 12 is a block diagram illustrating a schematic structure of a microfluidic system 1 according to an embodiment of the present inventive concept, and FIG. 13 is a flowchart illustrating a series of processes performed in the microfluidic system 1 according to an embodiment of the present inventive concept The microfluidic system 1 includes a reagent supply device 50, a binding-lysis chamber 117, rehydration chambers R1 to R6, nucleic acid amplification chambers P1 to P6, and a flow channel system (not shown) forming an integrated fluid flow between the reagent supply device 50, the binding-lysis chamber 117, the rehydration chambers R1 to R6, and the nucleic acid amplification chambers P1 to P6.

The reagent supply device 50 is a device able to store, transfer, and supply a sample as an examination target and a reaction reagent used for examining the sample, and includes a sample chamber in which the sample is injected, a plurality of reagent chambers, and a waste chamber in which the used reagent is discarded. The plurality of reagent chambers, for example, may be a lysis buffer chamber in which a lysis buffer for cell lysis is injected, and a washing buffer chamber in which a washing buffer is injected.

A series of processes, such as cell binding and DNA elution, is conducted in binding-lysis chamber 117. A plurality of particles for cell binding is disposed in the binding-lysis chamber 117. A diameter of each particle may be in a range of about 1 μm to about 1000 μm and an amount of each particle may be in a range of about 1 mg to about 100 mg. Each particle may have a random shape. Each particle may have a shape such as a bead, a sphere, a flat plate, a pillar, a sieve or filter, a gel, a layer, a fiber, or a combination thereof. Also, the particles may have magnetic properties. The particles may be formed, for example, of glass, silica, latex, or a polymeric material.

When the sample is injected into the binding-lysis chamber 117 from the sample chamber, cells are combined with the plurality of particles prepared in the binding-lysis chamber 117. Surfaces of the particles may include a material combined with the cell and the material may be specifically or nonspecifically combined with the cell. The material may include a substance, for example an antibody or a ligand, specifically combined with a substance on a surface of the cell. The material may be a hydrophobic material having a water contact angle ranging from about 70 degrees to about 90 degrees or a material having one or more amino groups. Examples of the hydrophobic material may be materials having a surface formed of octadecyltrichlorosilane ("OTS"), tridecafluorotetrahydrooctyl trimethoxysilane ("DTS"), octadecyldimethyl(3-trimethoxysilyl propyl)ammonium chloride ("OTC"), and polyethyleneiminetrimethoxysilane ("PEIM").

Next, a washing buffer is injected from the washing buffer chamber into the binding-lysis chamber 117 to wash the particles with the captured cells using a method of washing various debris or a buffer used during cell binding, and the particles may be dried by the injection of a gas such as air.

Thereafter, a lysis-buffer is injected from the lysis buffer chamber into the binding-lysis chamber 117, and external vibration is applied to the binding-lysis chamber 117 to vibrate the particles, lysing the cells so that nucleic acid may flow out of the binding-lysis chamber 117.

A cell lysate formed in the binding-lysis chamber 117 and a nucleic acid amplification reagent, for example, a PCR reagent, are mixed in rehydration chambers R1 to R6. The plurality of rehydration chambers R1 to R6 is included for a multiplex PCR, but the present inventive concept is not limited to the illustrated number of rehydration chambers. The cell lysate formed in the binding-lysis chamber 117 is distributed and introduced into each of the plurality of rehydration chambers R1 to R6. The nucleic acid amplification reagent may include, for example, a probe, a primer, an enzyme, or a combination thereof, and also may be disposed in a freeze-dried form in the rehydration chambers R1 to R6. The enzyme may include a polymerase. Rehydration chambers R1 to R6 may have a shape in which the freeze-dried nucleic acid amplification reagent and the cell lysate mix well with each other, and the mixture may then be extracted from rehydration chambers R1 to R6. The detailed shape of rehydration chambers R1 to R6 will further described below.

The nucleic acid amplification chambers may, for example, be a plurality of PCR chambers P1 to P6 and may correspond to the plurality of rehydration chambers R1 to R6. In each of the plurality of PCR chambers P1 to P6, a nucleic acid amplification reaction is performed on an amplification reaction mixture, for example a PCR mixture, which is introduced into the plurality of rehydration chambers R1 to R6.

Hereinafter, a PCR will be exemplified as a nucleic acid amplification reaction performed in the microfluidic system 1 and will be described by using expressions such as PCR chamber, PCR reagent, and PCR mixture. However, these expressions are described as examples of, respectively, an amplification chamber, a nucleic acid amplification reagent, and an amplification reaction mixture. In addition to the PCR, various other types of nucleic acid amplification reactions may be performed in the microfluidic system 1.

The microfluidic system 1 may include one or more metering chambers for quantifying an amount of a buffer supplied from the reagent supply device 50 to the binding-lysis chamber 117, and may also include one or more bubble trap chambers for removing bubbles which may be produced during a process of cell lysis.

The metering chambers may be disposed in a flow channel from the reagent supply device 50 toward the binding-lysis chamber 117 and in a flow channel from the binding-lysis chamber 117 toward rehydration chambers R1 to R6.

The bubble trap chambers may be disposed in the flow channel from the binding-lysis chamber 117 toward rehydration chambers R1 to R6 and/or in flow channels from rehydration chambers R1 to R6 toward PCR chambers P1 to P6.

Hereinafter, a detailed configuration of the microfluidic system 1 implementing the integrated flow channel system between the reagent supply device 50 and the plurality of chambers will be described.

Figure 14:
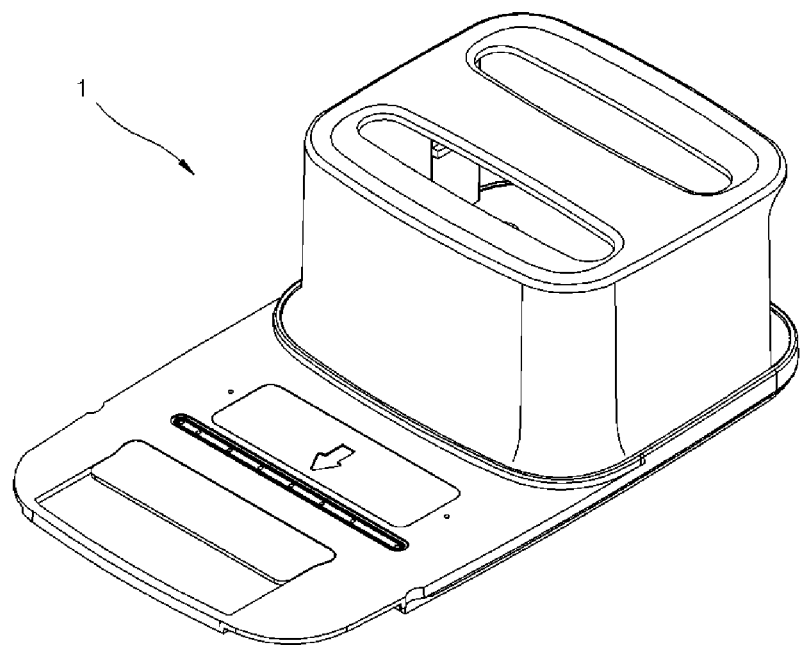
FIG. 14 is a perspective view illustrating a schematic external appearance of the microfluidic system.
Figure 15:
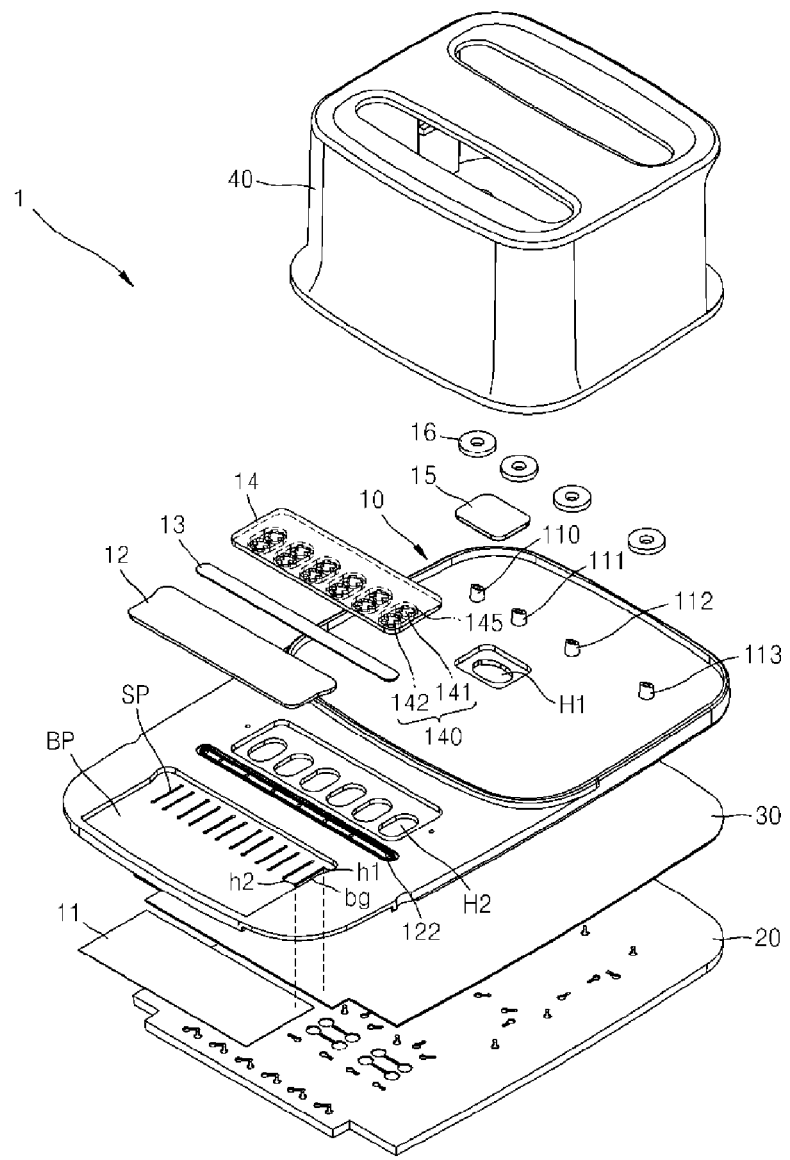
FIG. 15 is an exploded perspective view illustrating components constituting the microfluidic system of FIG. 14.

FIG. 14 is a perspective view illustrating a schematic external appearance of the microfluidic system 1 according to an embodiment of the present inventive concept, and FIG. 15 is an exploded perspective view illustrating components constituting the microfluidic system 1 of FIG. 14.

The microfluidic system 1 broadly includes a fluid flow part 10, a pneumatic part 20, and a membrane part 30, and may further include a guide part 40 for installation of the reagent supply device (not shown).

Figure 18:
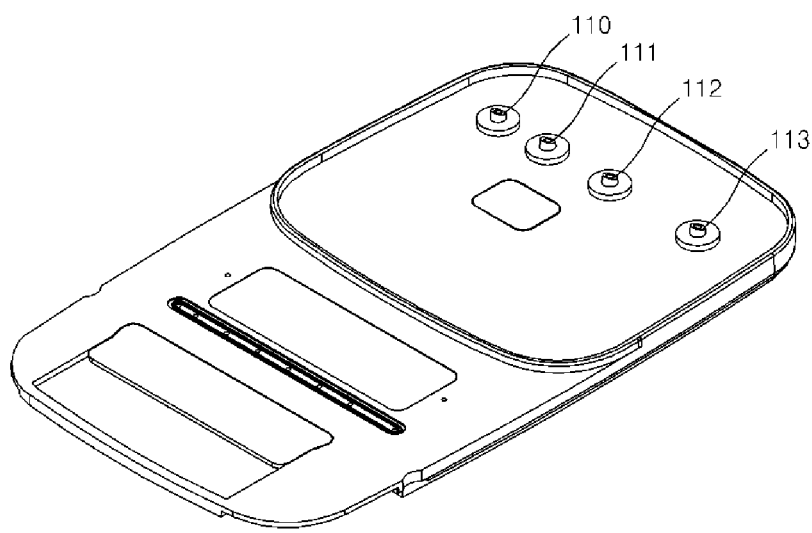
FIG. 18 illustrates needle-type inlets and an outlet formed on a top surface of the fluid flow part of the microfluidic system in FIG. 14.

As shown in FIG. 15, the fluid flow part 10 includes patterns, such as various through holes and inlets, constituting various channels, valves, and chambers that control the flow of a fluid to be examined. Fluid flow part 10 is formed of a transparent plastic material. For example, fluid flow part 10 may be formed of any one of polycarbonate ("PC"), polymethyl methacrylate ("PMMA"), polystyrene ("PS"), cyclic olefin copolymer ("COC"), polydimethylsiloxane ("PDMS"), and silicon, as a transparent polymer. Fluid flow part 10 includes inlets 110, 111, and 112 and outlet 113 connected to reagent supply device 50. Inlets 110, 111, and 112 and outlet 113 may be needle-shaped so as to allow a reagent to be released from reagent supply device 50 by breaking or rupturing a bottom surface of reagent supply device 50. FIG. 18 illustrates the needle-type inlets 110, 111, 112 and outlet 113 in detail. Fluid flow part 10 may also include a first through hole H1 forming a space defining, in part, the binding-lysis chamber 117 and a plurality of second through holes H2 forming spaces defining in part the plurality of rehydration chambers R1-R6. Also, a groove pattern (not shown) recessed so as to form spaces defining in part the plurality of PCR chambers P1-P6 may be included on a bottom surface of fluid flow part 10. Furthermore, a plurality of patterns (not shown) recessed so as to form microchannels implementing the flow channel system and a valve seat (not shown), and a protruding pattern for forming microvalves able to block the flows of the fluid passing the microchannels by pneumatic pressure applied from the pneumatic part 20, are formed on the bottom surface of fluid flow part 10.

Membrane part 30 is bonded to the bottom surface of fluid flow part 10 to form bottom surfaces of binding-lysis chamber 117, the plurality of rehydration chambers R1-R6, the metering chambers, the bubble trap chambers, and various other channels. Membrane part 30 is formed of an elastic material such as PDMS or silicone.

Pneumatic part 20 is for applying pneumatic pressure to fluid flow part 10 and is bonded to a bottom surface of membrane part 30. A plurality of ports for applying pneumatic pressure at a predetermined position of membrane part 30 are formed in pneumatic part 20. For example, the pneumatic pressure applied from the pneumatic part 20 may act to generate particle beating, such as bead beating, for a process of cell lysis in binding-lysis chamber 117 and to mix a PCR reagent and a cell lysate in rehydration chambers R1-R6. That is, membrane part 30 vibrates according to the pneumatic pressure applied from pneumatic part 20 and transfers vibration energy into binding-lysis chamber 117 or the rehydration chambers R1-R6. Also, pneumatic pressure applied from pneumatic part 20 may act to open and close the plurality of microvalves formed in fluid flow part 10. That is, membrane part 30 is in contact with the valve seat formed on the bottom surface of fluid flow part 10 to close the valves or is spaced apart from the valve seat to open the valves according to the pneumatic pressure applied by pneumatic part 20.

A plurality of particles (not shown) for cell binding is disposed in first through hole H1 formed in fluid flow part 10, and particle cover 15 covers first through hole H1.

Rehydration cover 14 covers the plurality of second through holes H2 formed in fluid flow part 10. The rehydration cover 14 may be the reagent container 1000 when the reagent container 1000 is implented on a rehydration chamber. Protrusions 145 are formed on rehydration cover 14 at positions corresponding to second through holes H2, grooves 140 that are recessed in a predetermined shape are formed on protrusions 145, and a PCR reagent (not shown) in a freeze-dried state is disposed in grooves 140.

The cell lysate requires various reagents to undergo a PCR. The various reagents may include a probe, a primer, an enzyme, or a combination thereof. Because these reagents may evaporate or activity of an enzyme may be degraded when the reagents are in a liquid phase, the reagents may be disposed in a freeze-dried state in rehydration cover 14. Grooves 140 formed in rehydration cover 14 respectively include the first well and the second well, that is, two subgrooves 141 and 142 separated from each other. The PCR reagent may be divided and disposed in the two subgrooves 141 and 142. For example, in each of the plurality of grooves 140, a nucleic acid-containing sample, for example, a sample including one or more of a probe and a primer, may be disposed in the first well (that is, the subgroove 141) and an enzyme may be disposed in the second well (that is, the subgroove 142). Also, in the first well, a polymerase-containing enzyme or a stabilizer may be disposed. An additive may be disposed in the first well and/or the second well.

A diameter of the protrusion 145 of the rehydration cover 14 may be formed to be slightly, e.g., about 10 μm, larger than a diameter of the second through hole H2, and the reason for this is to form a seal without using a separate adhesive. In the case where an adhesive is used, it is likely to cause problems with the freeze-dried reagent. Also, the rehydration cover 14 may be formed of a material having elasticity, for example, silicon or rubber, for more reliable sealing.

A PCR film 11 is formed on a bottom surface of PCR chamber P1-P6. That is, PCR film 11 is prepared at a position which may cover the groove pattern (not shown) recessed so as to form the spaces defining, in part, of PCR chambers P1-P6 on the bottom surface of fluid flow part 10.

A bridge pattern BP is formed on the top surface of the fluid flow part 10. Bridge pattern BP has a shape recessed from a top surface of fluid flow part 10 and forms a path in which the PCR mixture formed in rehydration chambers R1-R6 moves to PCR chambers P1-P6. Bridge pattern BP constitutes a channel for guiding PCR mixture that may flow over the top surface of fluid flow part 10 when the PCR mixture formed in rehydration chambers R1-R6 moves to PCR chambers P1-P6. Bridge pattern BP includes a plurality of subpatterns SP. Each of the plurality of subpatterns SP includes a hole h1 penetrating fluid flow part 10 to face membrane part 30, a hole h2 penetrating fluid flow part 10 to face PCR film 11, and a bridge groove bg connecting two holes h1 and h2 and recessed from the top surface of fluid flow part 10. Hole h2, which will be further described below, forms an inlet hole toward PCR chambers P1-P6 or an outlet hole from PCR chambers P1-P6. Furthermore, bridge cover 12 covers the plurality of subpatterns SP and is disposed on the top surface of fluid flow part 10. Ultrasonic welding energy directors (not shown) for ultrasonic joining with fluid flow part 10 may be formed on bridge cover 12. Alternatively, ultrasonic welding energy directors may be formed on fluid flow part 10, for example, near holes h1 and h2 and recessed bridge groove bg.

Vent channel 122 and vent cover 13 covering vent channel 122 are disposed on the top surface of fluid flow part 10. Vent channel 122 may release excess fluid for storage in a predetermined space when the fluid continuously flows after filling a predetermined chamber, such as when the flow of the fluid is not accurately detected. Vent channel 122 as illustrated in FIG. 15 may comprise a region recessed in a predetermined shape and a plurality of vent holes formed therein.

A plurality of recessed pattern (not shown) for forming the metering chambers and bubble trap chambers may be formed on the bottom surface of fluid flow part 10. For example, the recessed patterns may form one or more metering chambers for quantifying the amount of the lysis buffer supplied from the lysis buffer chamber of reagent supply device 50, and one or more bubble trap chambers for removing bubbles, generated in the binding-lysis chamber during the cell lysis. The recessed patterns may also form the plurality of metering chambers for quantifying an amount of cell lysate formed in the binding-lysis chamber and distributing the cell lysate into the plurality of rehydration chambers R1-R6.

A process of forming an assembly as in FIG. 14 is described below. First, fluid flow part 10 is prepared and PCR film 11 is attached to the bottom surface of fluid flow part 10 using any suitable adhension method, including ultrasonic welding, an adhesive, or tape. Bridge cover 12 and vent cover 13 are also attached to the top surface of fluid flow part 10 by any suitable adhension method.

The bottom surface of fluid flow part 10, i.e., the surface to be bonded to membrane part 30, is coated with $SiO_2$ to a thickness of about 3,000 Å.

Pneumatic part 20 is prepared and each surface of pneumatic part 20 and membrane part 30 to be bonded is plasma treated. Pneumatic part 20 and membrane part 30 are bonded to each other.

A bonding surface of $SiO_2$-coated fluid flow part 10 and a bonding surface of pneumatic part 20 bonded to membrane part 30 are plasma treated, and $SiO_2$-coated fluid flow part 10 and pneumatic part 20 bonded to membrane part 30 are bonded to each other.

Particles are injected into first through hole H1, forming the binding-lysis chamber, and particle cover 15 is bonded to first through hole H1 by any suitable adhension method.

O-rings 16 are inserted over each of inlet 110, 111, and 112 and outlet 113, guide part 40 is aligned with a top portion of fluid flow part 10, and guide part 40 and fluid flow part 10 are then bonded by any suitable adhesion method.

Figure 23A:
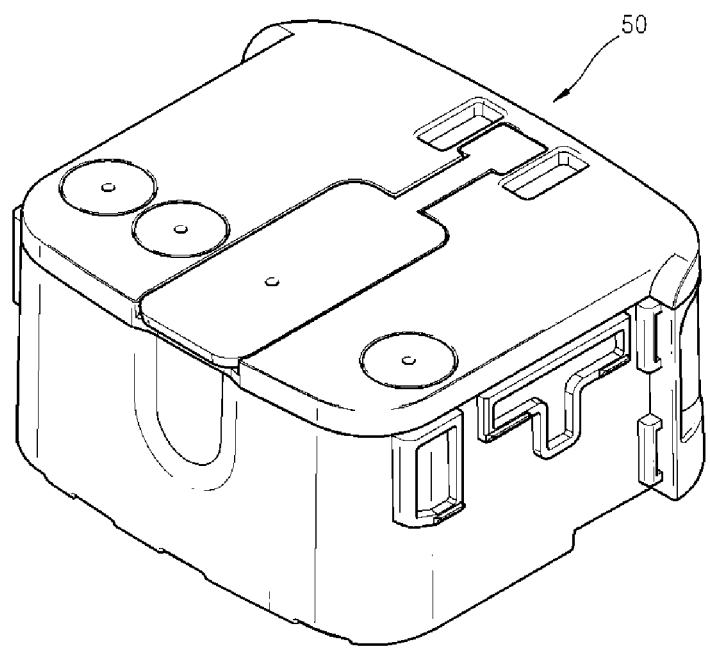
FIGS. 23A through 23C illustrate external structures of a reagent supply device.

Reagent supply device 50 (as shown in FIG. 23A) is installed by being inserted into guide part 40. O-rings 16 inserted between reagent supply device 50 and fluid flow part 10 may act to prevent leakage of a solution.

Rehydration cover 14, in which freeze-dried PCR reagent is disposed, is assembled on fluid flow part 10.

Figure 16:
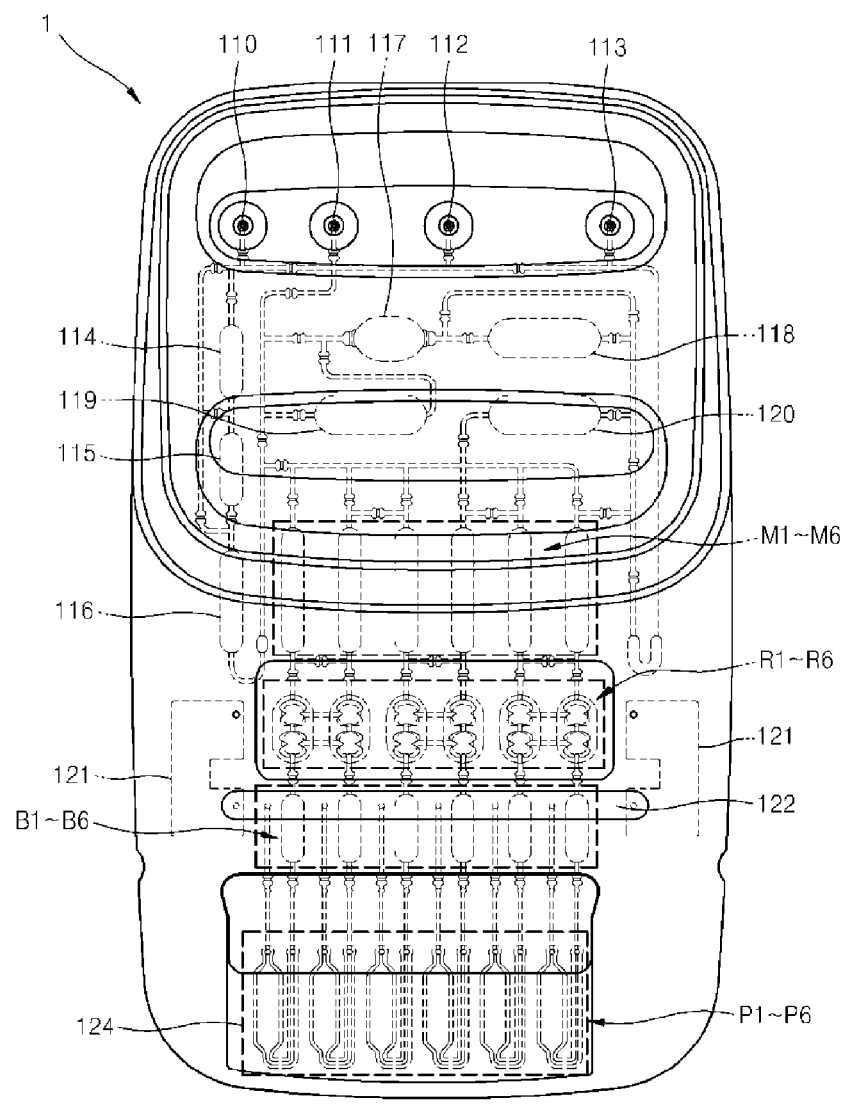
FIG. 16 is a plan view illustrating the microfluidic system of FIG. 14.

FIG. 16 is a plan view illustrating the microfluidic system 1 of FIG. 14.

Reagents, including the lysis buffer, the washing buffer, and the sample, are respectively injected from reagent supply device 50 through a port which includes inlets 110, 111, and 112 and outlet 113. As illustrated in FIG. 15, because inlets 110, 111, and 112 and outlet 113 are tilted toward a direction of insertion when reagent supply device 50 is inserted from an opened direction of guide part 40, inlets 110, 111, and 112 and outlet 113 may be inserted into reagent supply device 50 when it slides over the needle shape of inlets 110, 111, 112 and outlet 113. In this manner inlets 110, 111, and 112 and outlet 113 may act to prepare paths by penetrating a membrane constituting the bottom surface of the reagent supply device 50 so as to allow the reagent stored therein to be released.

Metering chambers 114, 115, and 116 are for quantifying the lysis buffer introduced through inlet 110. For example, NaOH may be used as a lysis buffer for cell lysis and an enrichment effect may increase when the lysis buffer having a volume as small as possible is used and is transferred to PCR chambers P1-P6 without loss. Metering chambers 114, 115, and 116 may have different volumes from one another. For example, metering chambers 114, 115, and 116 may have a volume of about 8 μl, about 8 μl, and about 12 μl, respectively. Because about 12 μl of the lysis buffer may be used when only metering chamber 116 is used, the metering chamber 116, for example, may be used in the case where two of the six PCR chambers P1-P6 are used, each PCR chamber having a volume of about 4 μl. When metering chambers 115 and 116 are simultaneously used, about 20 μl of the lysis buffer may be used, and thus, four of the six PCR chambers P1-P6 may be used. When metering chambers 114, 115 and 116 are simultaneously used, about 28 μl of the lysis buffer may be used, and thus, all six PCR chambers P1-P6 may be used. About 4 μl of a dead volume may exist even in the case where any combination of metering chambers 114, 115, and 116 is used and thus, PCR chambers P1-P6 may be filled even in the case where some of the sample is lost. The number of metering chambers and the volume of each are exemplary and may be variously changed.

In a channel connected to binding-lysis chamber 117, a weir having a gap of about 20 μm may be formed from a bottom of the channel to a ceiling thereof in order for the particles injected into binding-lysis chamber 117 for cell binding not to be released.

In one embodiment, bubble trap chambers 118, 119, and 120 each have a volume of about 28 μl. Bubble trap chambers 118, 119, and 120 reciprocate the buffer in the case where cells having a low concentration are attempted to be analyzed, and also remove bubbles which may be generated after the cell lysis through the movement of membrane part 30. That is, bubble trap chambers 118, 119, and 120 reciprocate an elution buffer in a forward direction (bubble trap chamber 119→binding-lysis chamber 117→bubble trap chamber 118) and a backward direction (bubble trap chamber 118 →binding-lysis chamber 117→bubble trap chamber 119) centered on binding-lysis chamber 117. A buffer that is the same as the lysis buffer may be used as the elution buffer and the buffer may be used as the elution buffer by being further added after the lysis. In one embodiment, Bubble trap chambers 118, 119, and 120 may have a volume which may entirely accommodate a maximum volume of about 28 μl during the reciprocation of the buffer. Bubble trap chamber 120 removes bubbles of the cell lysate being subjected to an entire DNA elution process to prevent various errors due to the bubbles during a subsequent process. The number of bubble trap chambers and the volume of each are exemplary and may be variously changed.

Two confining chambers 121 positioned at both sides of vent channel 122 act to confine the fluid containing the reagent and the sample so as not to flow out through vent channel 122 due to potential system errors. That is, when PCR chambers P1-P6 are accurately filled and the flow of the fluid is accurately stopped by being detected by the system, the fluid does not flow out through the vent channel 122. However, when the flow of the fluid is not detected after PCR chambers P1-P6 are filled with the fluid and the fluid continuously flows, the fluid may flow out through vent channel 122 to be collected in confining chambers 121 at both sides thereof.

Domain 124, as a top portion of PCR chambers P1-P6, is an optical window for observing changes in an amount of fluorescence according to the process of the PCR. Domain 124 is prepared to be thinner than the surrounding area so as to allow as small amount of fluorescence as possible to be transmitted out. Metering chambers M1-M6, in one embodiment each having a volume of about 4 μl, may distribute and store the lysate passing through bubble trap chamber 120 in amounts of about 4 μl, respectively. The cell lysate stored in the metering chambers M1-M6 is respectively injected into rehydration chambers R1-R6 and mixed with the probe, the primer, the enzyme, or a combination thereof, is freeze-dried, and stored in rehydration chambers R1-R6 by the movement of membrane part 30 to prepare a PCR mixture.

A PCR, the last operation of an analysis process using the microfluidic system 1, is performed in PCR chambers P1-P6. The PCR mixture passing through rehydration chambers R1-R6 passes through bubble trap chambers B1-B6, and is then injected into PCR chambers P1-P6. Because, in one embodiment, about 4 μl of the PCR mixture is used to fill an entire region of the channels connected to PCR chambers P1-P6 without bubbles as well as PCR chambers P1-P6, a volume actually participating in the PCR may be about 2.5 μl.

Figure 17A:
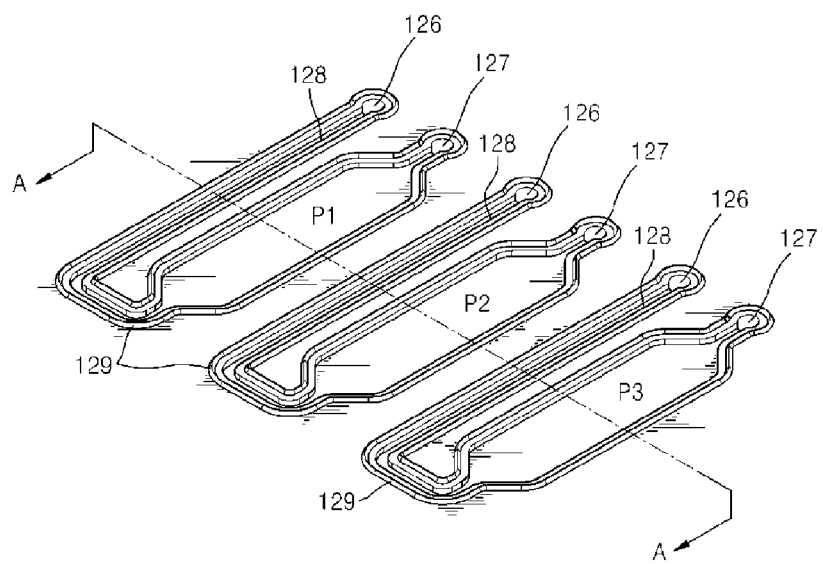
FIG. 17A illustrates groove patterns for forming spaces of PCR chambers formed on a bottom surface of a fluid flow part of the microfluidic system in FIG. 14.
Figure 17B:
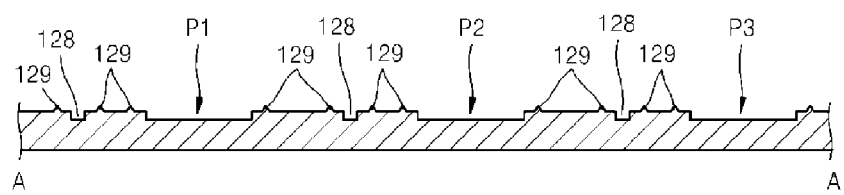
FIG. 17B is a cross sectional view taken along line A-A in FIG. 17A.

FIG. 17A illustrates groove patterns for forming spaces of PCR chamber P1-P6 formed on the bottom surface of fluid flow part 10 of FIG. 15, and FIG. 17B is a cross-sectional view taken along line A-A in FIG. 17A.

For convenience, FIGS. 17A and 17B exemplarily illustrate only three PCR chambers P1-P3. The other three PCR chambers P4-P6 have the same structure. An inlet hole 126, an inlet channel 128, and an outlet hole 127 are connected to each of PCR chambers P1-P6. The PCR mixture introduced through inlet hole 126 flows in along inlet channel 128 to fill each PCR chamber P1-P6 and then flows out of each PCR chamber P1-P6 through outlet hole 127. Inlet hole 126 and outlet hole 127 are not disposed on opposite sides with respect to PCR chambers P1-P6, but are disposed on the same side for the miniaturization of the microfluidic system 1 and the maximization of a fluorescence signal. Thus, since depths of PCR chambers P1-P6 are secured in a predetermined range, a higher fluorescence signal may be obtained and a deviation in temperatures between PCR chambers P1-P6 may be reduced by arranging the six PCR chambers P1-P6 as close to one another as possible. PCR film 11 is attached to the bottom surface of fluid flow part 10 in order to form bottom surfaces of PCR chambers P1-P6 and effectively transfer heat. Ultrasonic welding or any suitable adhesion method may be used to attach PCR film 11 to the bottom surface of fluid flow part 10. Energy directors 129 having a height of about 100 μm may be formed for the ultrasonic welding. As illustrated in FIG. 17B, the energy directors 129 may be formed at a predetermined interval from inlet channel 128 and corners of PCR chambers P1-P6.

Figure 19A:
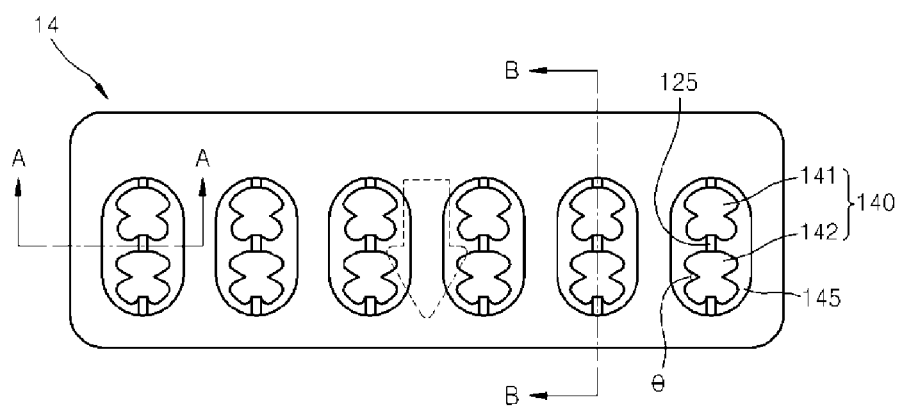
FIG. 19A is a plan view illustrating a structure of a rehydration cover.
Figure 19B:
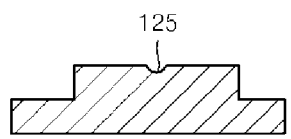
FIG. 19B is a cross sectional view taken along line A-A in FIG. 19A.
Figure 19C:
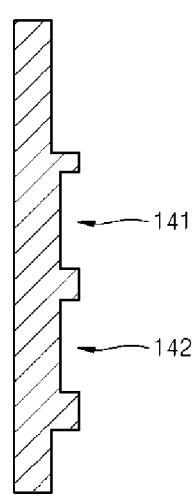
FIG. 19C is a cross sectional view taken along line B-B in FIG. 19A.

FIG. 19A is a plan view illustrating a structure of rehydration cover 14, FIG. 19B is a cross-sectional view taken along line A-A in FIG. 19A, and FIG. 19C is a cross-sectional view taken along line B-B in FIG. 19A.

Rehydration cover 14 is for forming the six rehydration chambers R1-R6 and includes six protrusions 145 corresponding to six through holes forming the spaces of rehydration chambers R1-R6. Recessed groove 140 is formed in each protrusion 145 and each groove includes the first well and the second well which are two subgrooves 141 and 142. A sample including a probe, a primer, or a combination thereof is freeze-dried and contained in subgroove 141, and a sample including an enzyme is freeze-dried and contained in subgroove 142. An arrow represents a direction of the movement of the fluid. Subgrooves 141 and 142 are connected through microchannel 125. The cell lysate is introduced from an upper side of subgroove 141 to fill subgroove 141 and then passes through microchannel 125 to fill subgroove 142. A shape of subgrooves 141 and 142 is formed so as to allow the cell lysate to be easily released without leaving a residue in subgrooves 141 and 142 after the cell lysate fills subgrooves 141 and 142 without bubbles and is mixed with the PCR reagents by the movement of membrane part 30. The shape of subgrooves 141 and 142 may be determined through hydrodynamic analysis in consideration of surface properties of the inner surfaces of subgrooves 141 and 142 and solution properties of the nucleic acid lysate. As illustrated in FIG. 19A, sides of subgrooves 141 and 142 may have a curved shape and a width of a center portion thereof may be the smallest width of the subgroove. An external angle θ formed by corners of the narrow center of subgrooves 141 and 142 may be in a range of about 30 degrees to about 90 degrees.

Figure 20A:
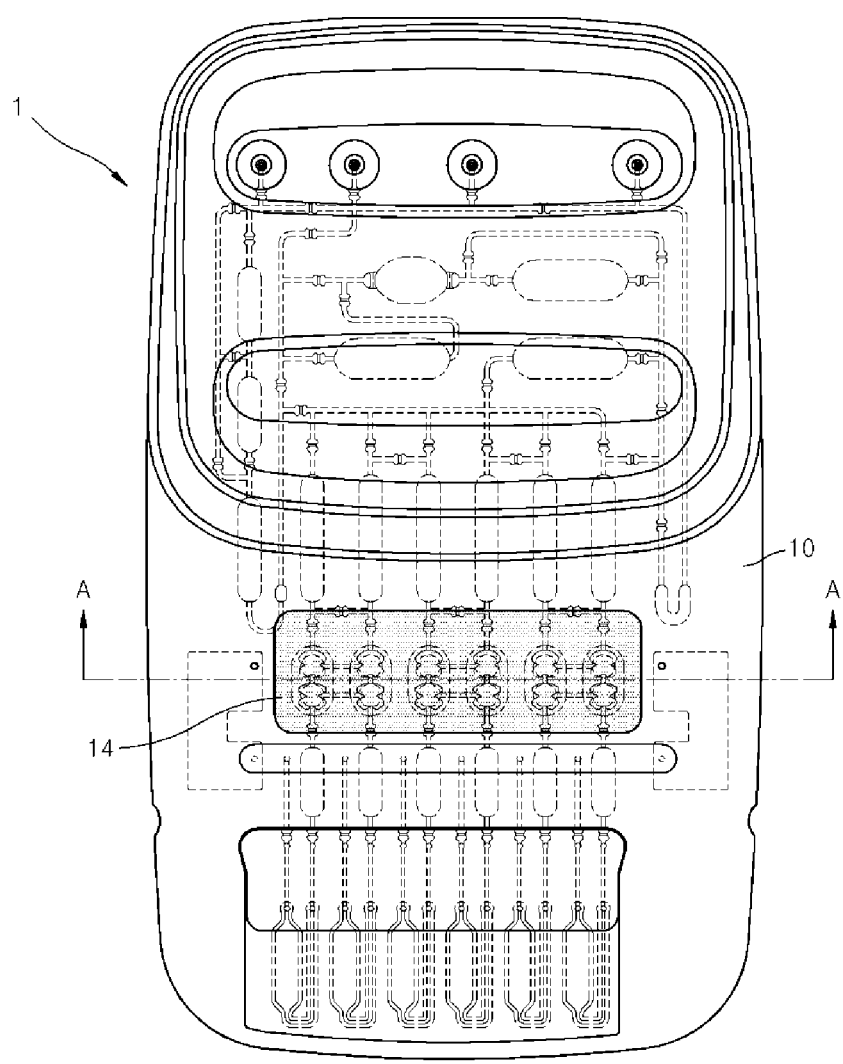
FIG. 20A is a plan view illustrating a state in which a rehydration cover and a fluid flow part are combined.
Figure 20B:
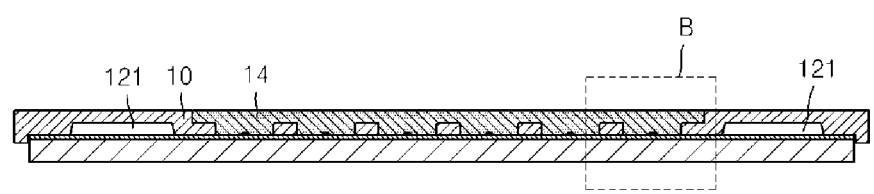
FIG. 20B is a cross sectional view taken along line A-A in FIG. 20A.
Figure 20C:
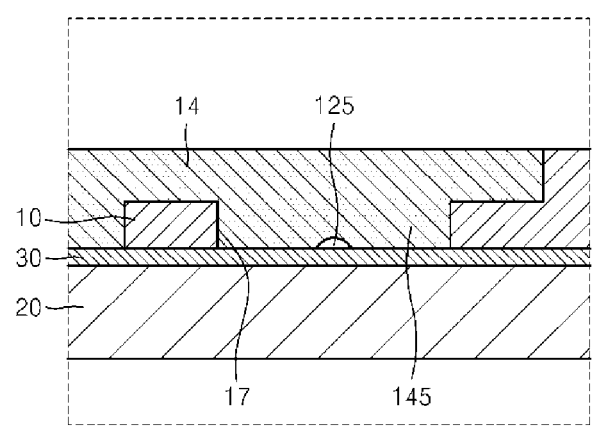
FIG. 20C is an enlarged view illustrating a detailed portion of FIG. 20B.

FIG. 20A is a plan view illustrating a state in which rehydration cover 14 and fluid flow part 10 are combined, FIG. 20B is a cross-sectional view taken along line A-A in FIG. 20A, and FIG. 20C is an enlarged view illustrating a detailed portion of FIG. 20B.

In one embodiment, a separate adhesive is not used during the combination of rehydration cover 14 and fluid flow part 10, but properties of materials constituting each component are used to form a seal. An adhesive may cause problems with the freeze-dried PCR reagents. As described above, the seal may be formed by forming the diameter of protrusion 145 of rehydration cover 14 to be slightly larger than the diameter of second through hole H2 in which protrusion 145 is inserted in fluid flow part 10. FIG. 20C illustrates a position of microchannel 125 connecting subgrooves 141 and 142 after the completion of the combination, and when the combination is accurately completed as above, a leakage along an interface between fluid flow part 10 and rehydration cover 14 may not occur and the solution may only move along microchannel 125.

Figure 21A:
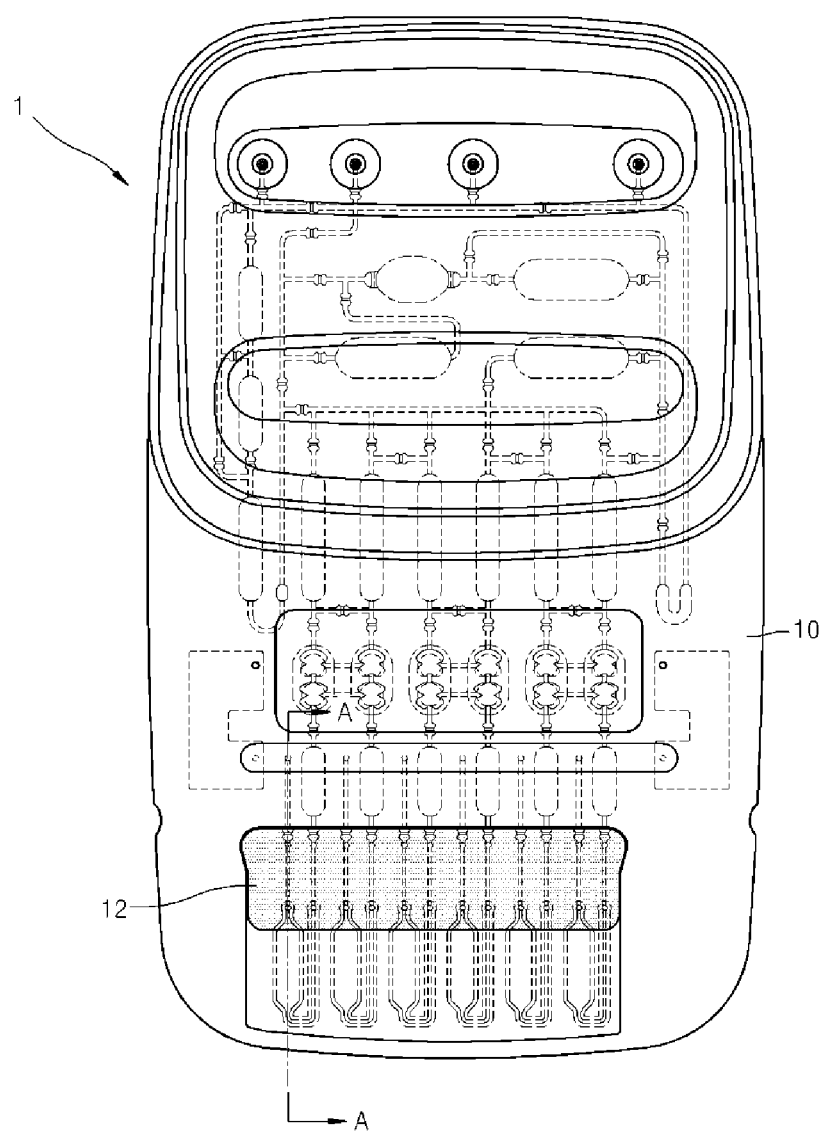
FIG. 21A is a plan view illustrating a state in which a bridge cover and the fluid flow part are combined.
Figure 21B:
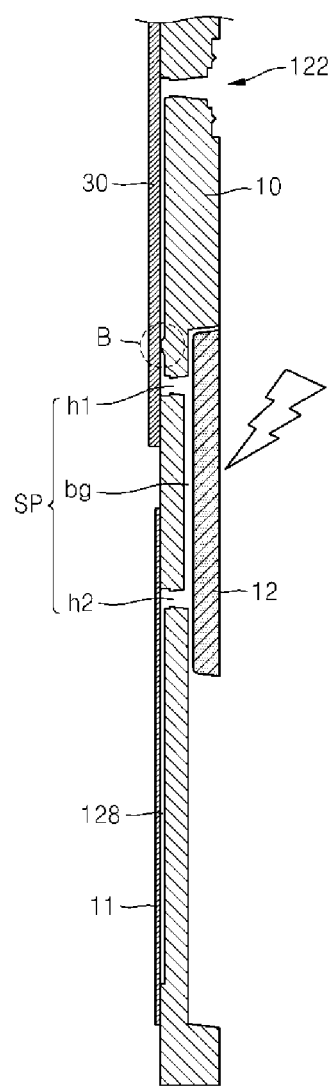
FIG. 21B is a cross sectional view taken along line A-A in FIG. 21A.
Figure 21C:
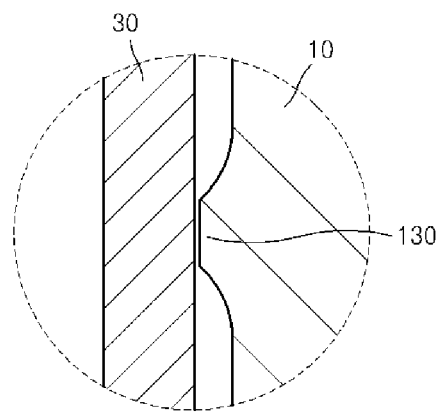
FIG. 21C is an enlarged view illustrating a detailed portion of FIG. 21B.

FIG. 21A is a plan view illustrating a state in which bridge cover 12 and fluid flow part 10 are combined, FIG. 21B is a cross sectional view taken along a line A-A in FIG. 21A, and FIG. 21C is an enlarged view illustrating a detailed portion of FIG. 21B.

Bridge cover 12 together with bridge pattern BP formed on the top surface of fluid flow part 10 enables the vertical movement of the fluid. Bridge pattern BP includes the plurality of subpatterns SP, and each subpattern SP includes hole h1 penetrating fluid flow part 10 to face membrane part 30, hole h2 penetrating fluid flow part 10 to face PCR film 11, and recessed bridge groove bg connecting two holes h1 and h2. In the cross section of FIG. 21B, hole h2 becomes the inlet hole (see 126 in FIG. 17A) connected to inlet channel 128 toward PCR chambers P1-P6. Because membrane part 30 is attached to the bottom surface of fluid flow part 10 and the bottom surfaces of PCR chambers P1-P6 are formed of PCR film 11, a channel connected to membrane part 30 and PCR film 11 may be difficult to form. For the flow of the fluid toward the PCR chambers P1-P6, the fluid passing through bubble trap chambers B1-B6 of fluid flow part 10 moves above fluid flow part 10 through hole h1 and flows into inlet channel 128 toward PCR chambers P1-P6 through hole h2 while moving along bridge groove bg. Bridge cover 12 may be welded to the top portion of fluid flow part 10 forming bridge pattern BP through ultrasonic welding.

Bridge groove bg also acts as a channel for detecting the flow of the solution which fills PCR chambers P1-P6 and flows out therefrom. That is, when the flow of the solution is detected in bridge groove bg, the further introduction of the PCR mixture into PCR chambers P1-P6 is stopped.

FIG. 21C illustrates portion B of FIG. 21B in detail. The starting and stopping of the flow of the fluid is controlled according to the attachment or detachment of membrane part 30 to valve seat 130. Valve seat 130 is detached from membrane part 30 when no external pressure is applied to membrane part 30. That is, a microvalve is in a state of being opened. Such a configuration embodies a normally-open type valve, and is different from a normally-closed type in which membrane part 30 and valve seat 130 are in contact with each other when no external pressure is applied to membrane part 30. With respect to the normally-closed type valve, membrane part 30 may be naturally fixed to valve seat 130 due to a chemical or physical reaction when the microvalve does not operate for a prolonged period of time. Therefore, when the microvalve is not used for a prolonged period of time, an initialization for detaching membrane part 30 from valve seat 130 may be necessary. In the present embodiment, the microvalve is more easily realized by using a normally-open type valve.

When filling PCR chamber, the valve in portion B is opened. That is, membrane part 30 is not allowed to be in contact with valve seat 130 to form an exhaust path toward vent channel 122, and when the flow of the solution in bridge groove bg under bridge cover 12 is detected to stop the introduction of the PCR mixture, the valve in portion B is closed.

Figure 22A:
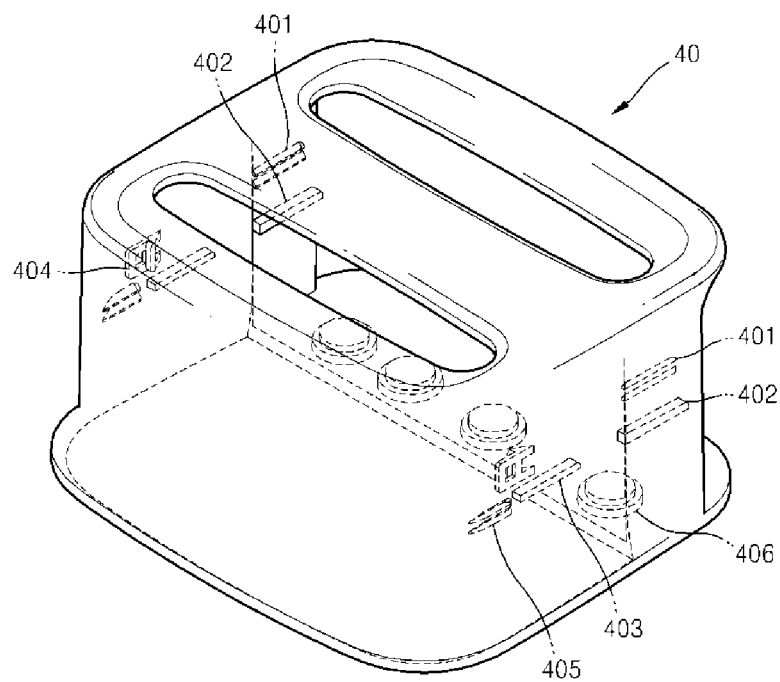
FIGS. 22A through 22C illustrate detailed structures of a guide part in which a reagent supply device is installed.
Figure 22B:
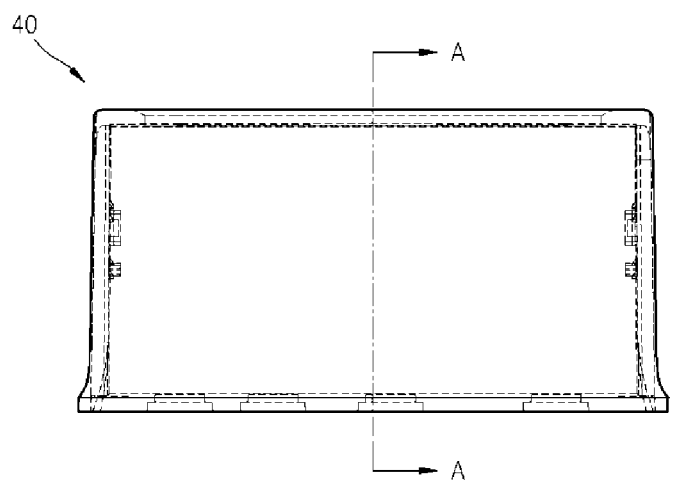
Figure 22C:
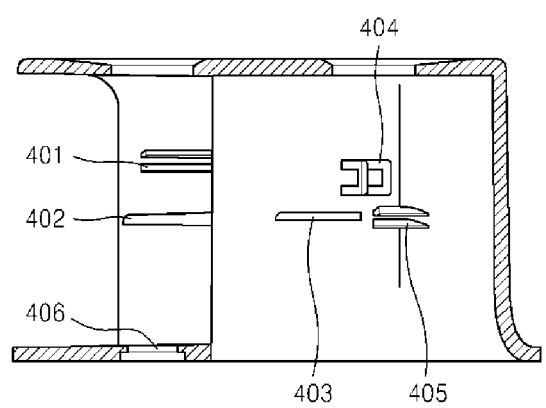
Figure 23B:
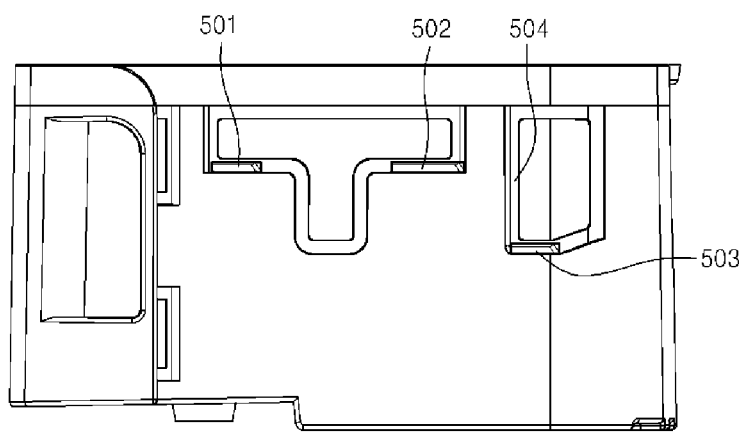
Figure 23C:
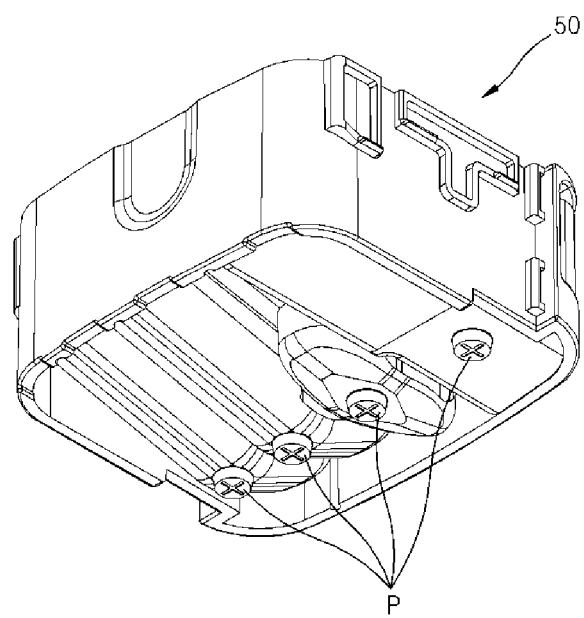

FIGS. 22A through 22C illustrate detailed structures of guide part 40 in which reagent supply device 50 is installed, and FIGS. 23A through 23C illustrate external structures of reagent supply device 50.

Horizontal axes of upper surfaces of structures 401 and 404 act as a support for sliding structures 501 and 502 thereon during insertion of reagent supply device 50, and for preventing damage in a case where membrane part 30 is punctured by being pressed downward. When reagent supply device 50 is accurately inserted up to a particular position, hooks disposed on a vertical axis of the structures 404 are fastened with the structures 504 to thus prevent reagent supply device 50 from being pushed backward again in an inserted direction. As illustrated in FIG. 23C, destruction patterns P are formed on the bottom surface of reagent supply device 50 and are broken by needle-shaped inlets 110, 111, and 112 and outlet 113 illustrated in FIG. 15 to allow the reagent and the sample to flow in and flow out of reagent supply device 50. In the operation in which destruction patterns P are being penetrated, structures 501, 502, and 503 are combined with structures 402, 403, and 405 to prevent the reagent supply device 50 from being raised upward.

Figure 24A:
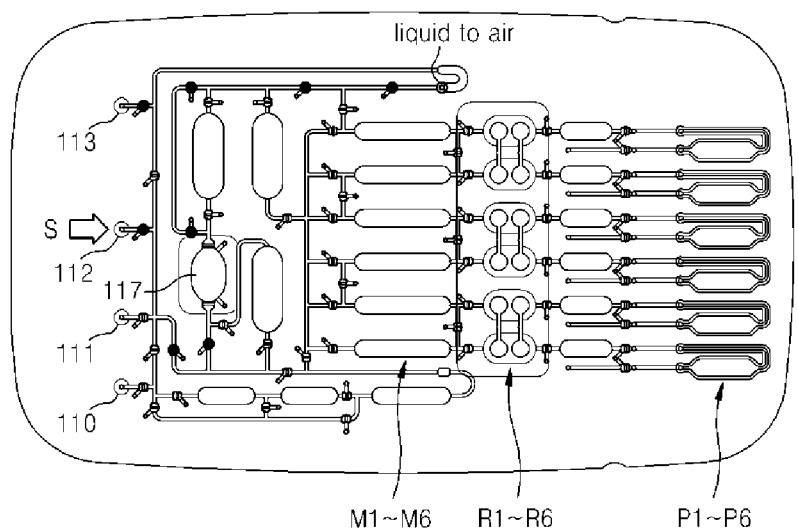
FIGS. 24A through 24T are plan views illustrating processes of performing operations according to the flowchart of FIG. 13 with valve operations used in the movement of a fluid in the microfluidic system.
Figure 24B:
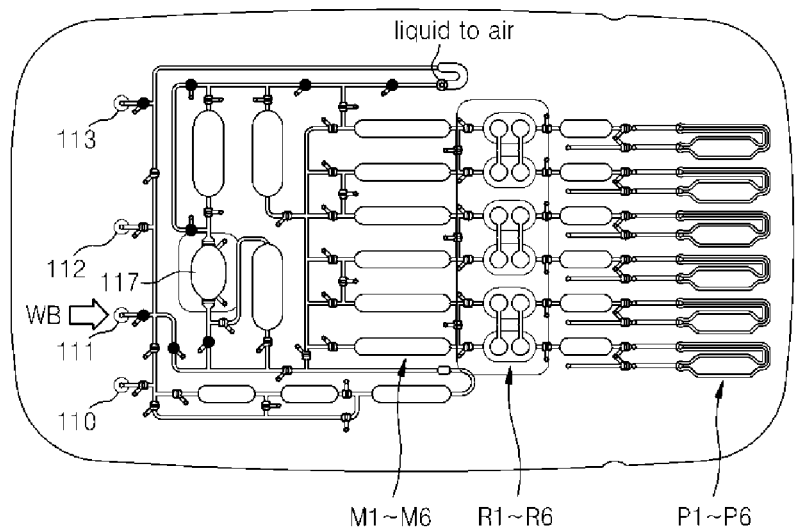
Figure 24C:
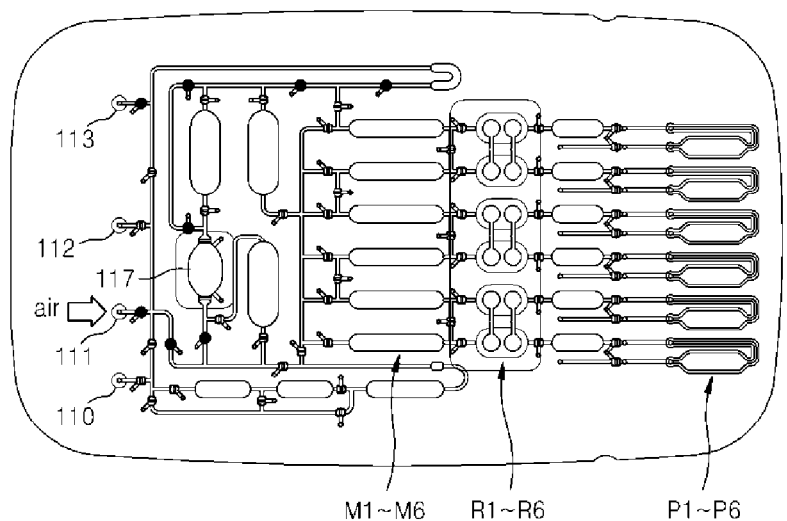
Figure 24D:
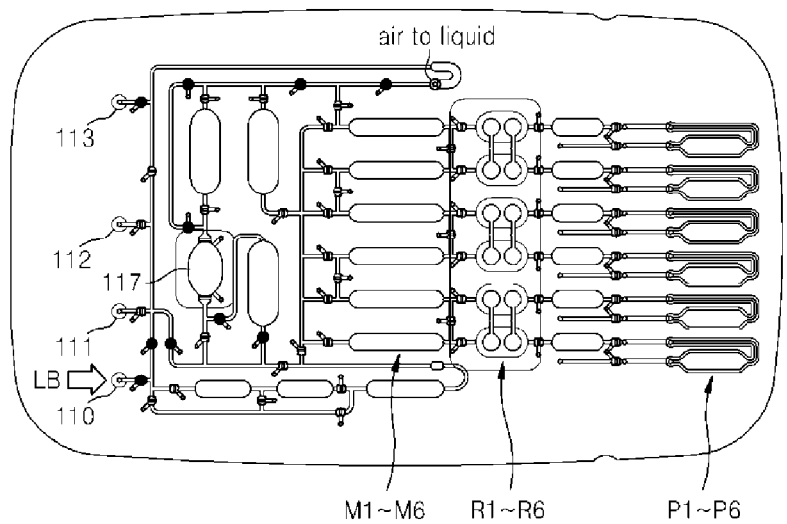
Figure 24E:
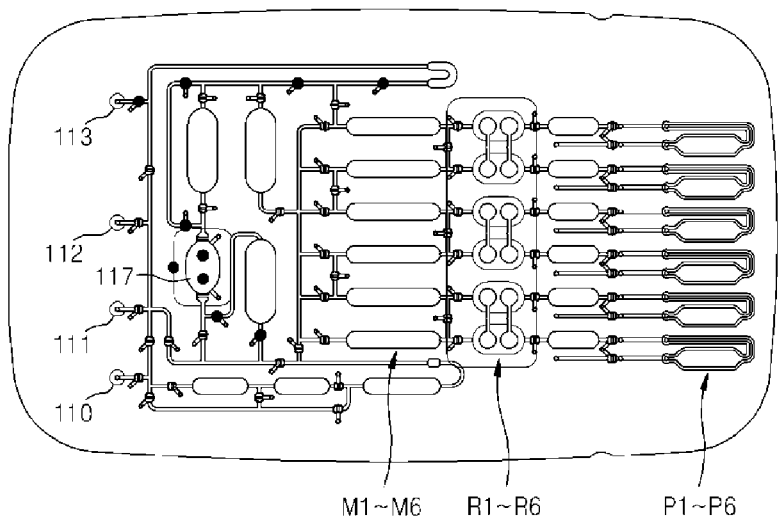
Figure 24F:
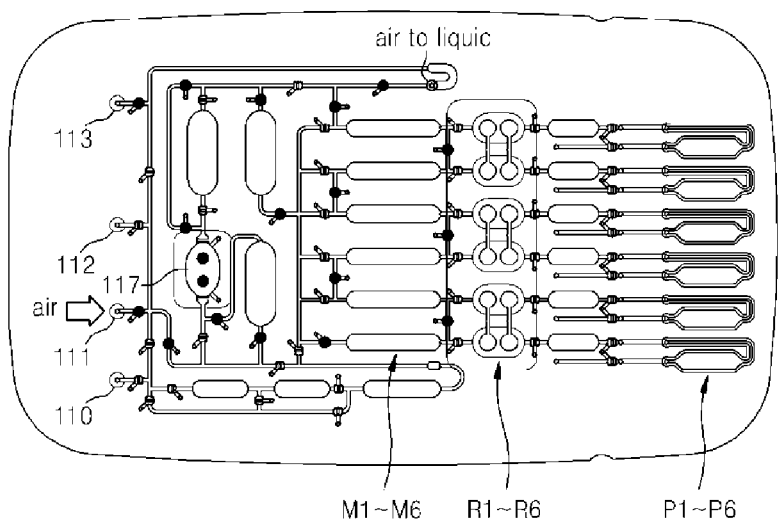
Figure 24G:
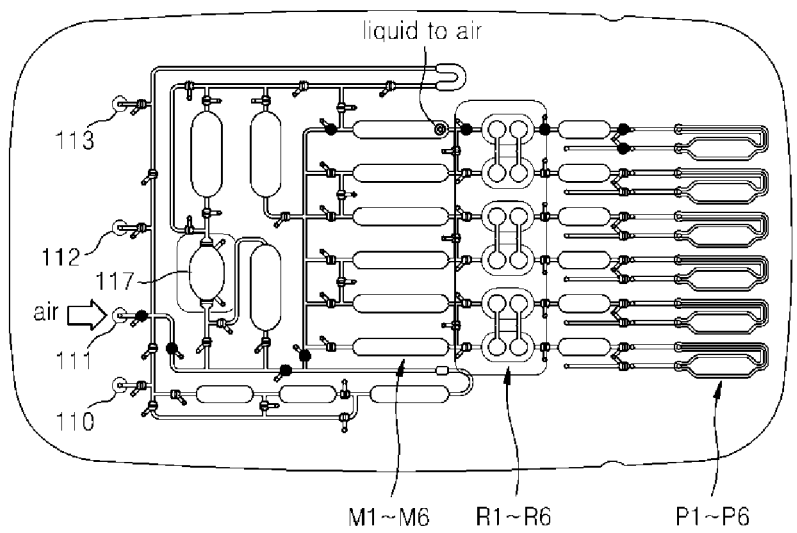
Figure 24H:
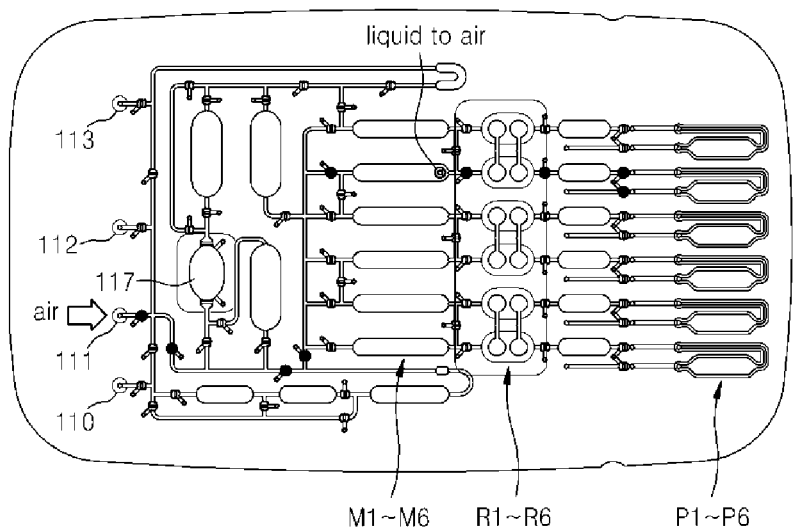
Figure 24I:
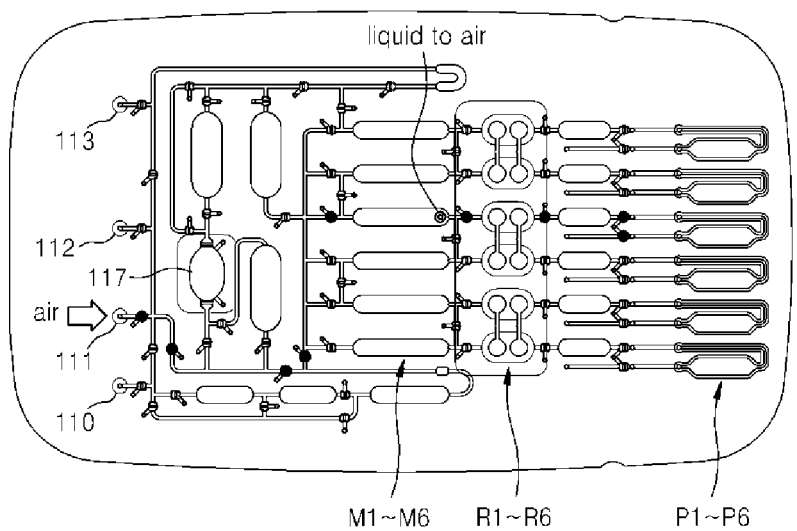
Figure 24J:
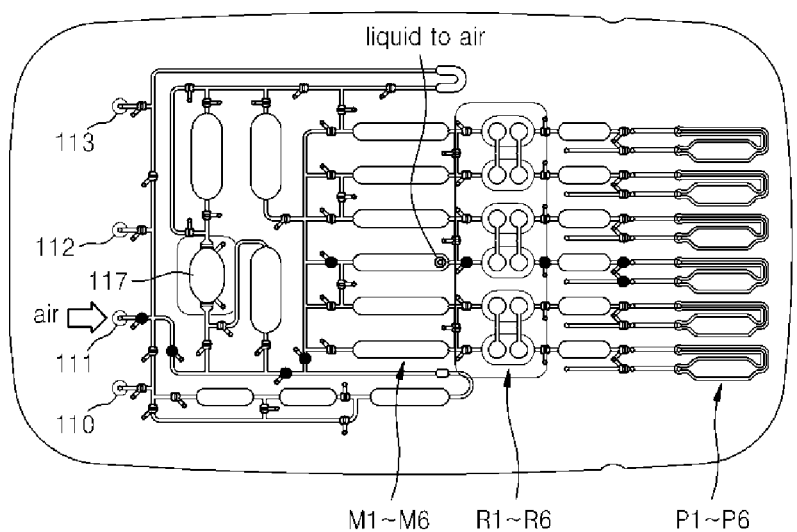
Figure 24K:
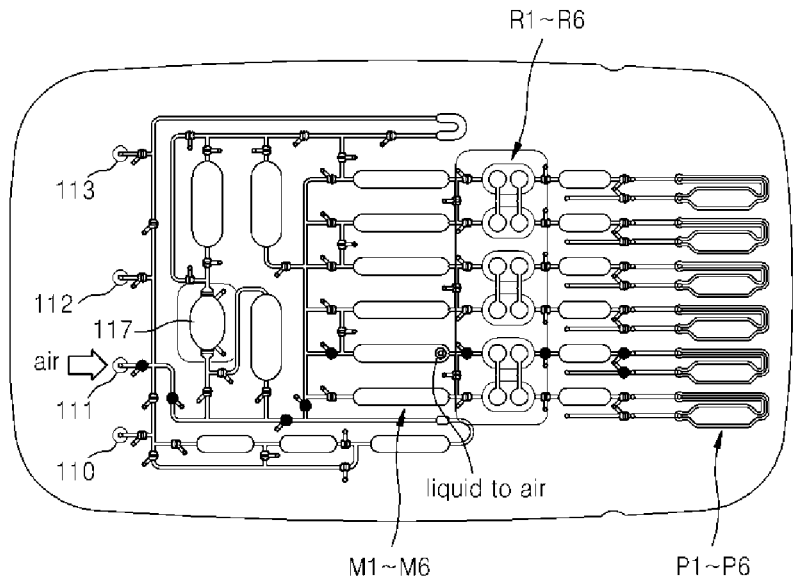
Figure 24L:
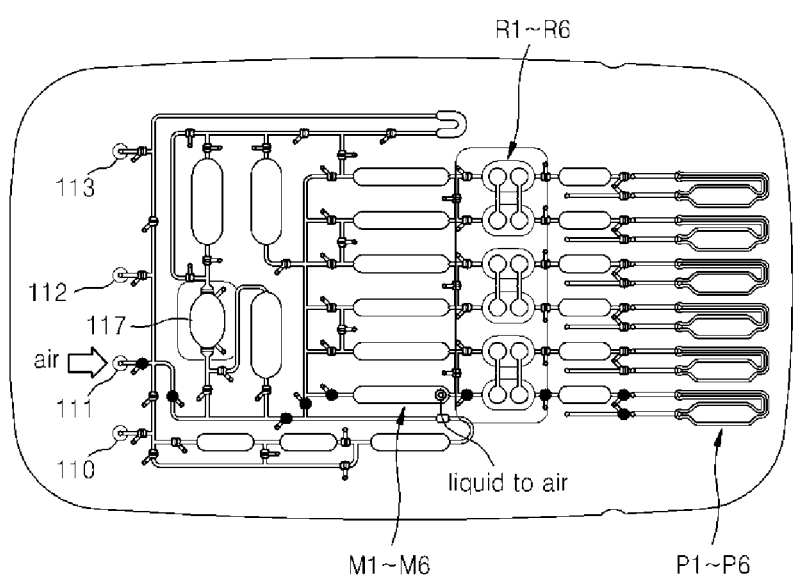
Figure 24M:
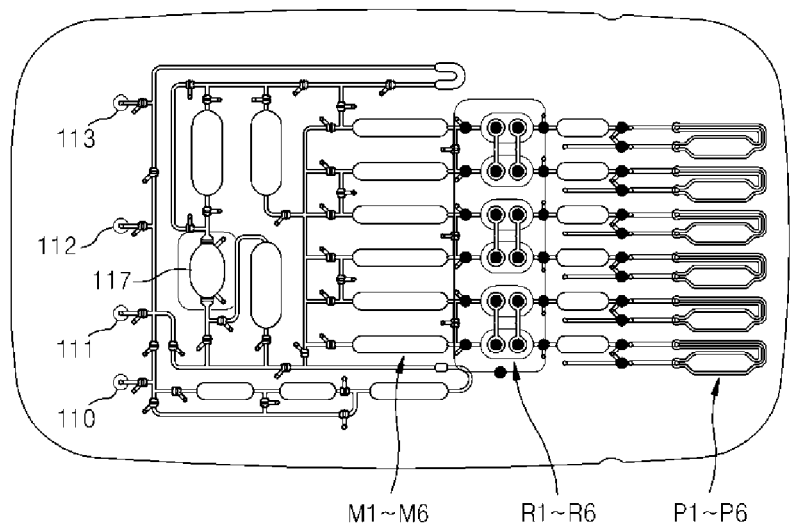
Figure 24N:
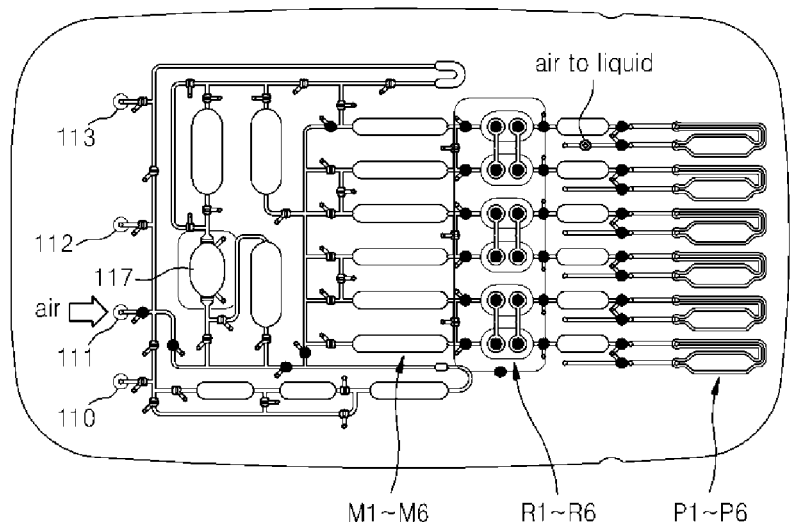
Figure 24O:
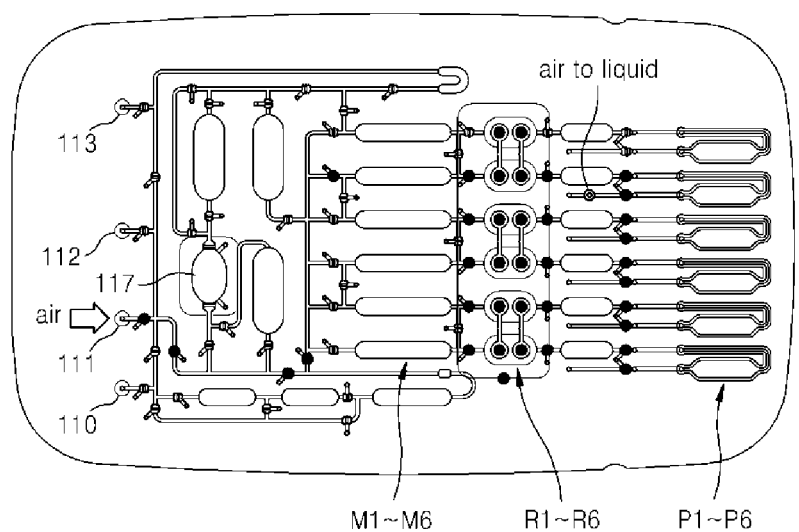
Figure 24P:
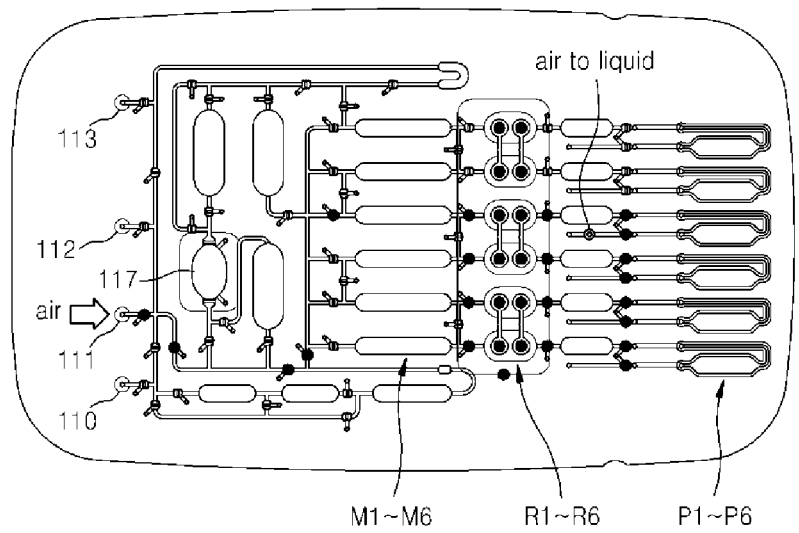
Figure 24Q:
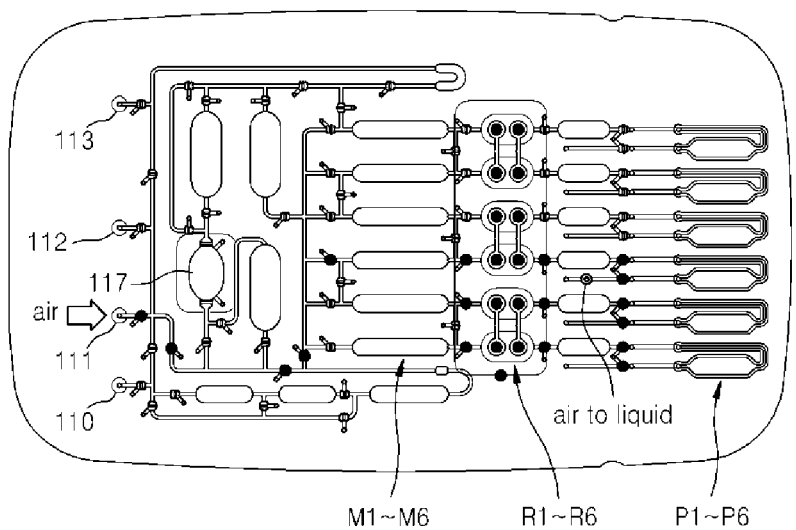
Figure 24R:
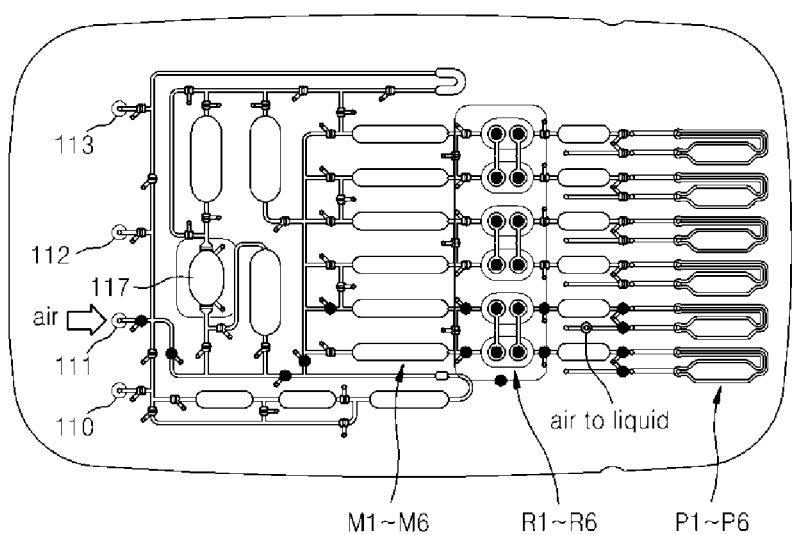
Figure 24S:
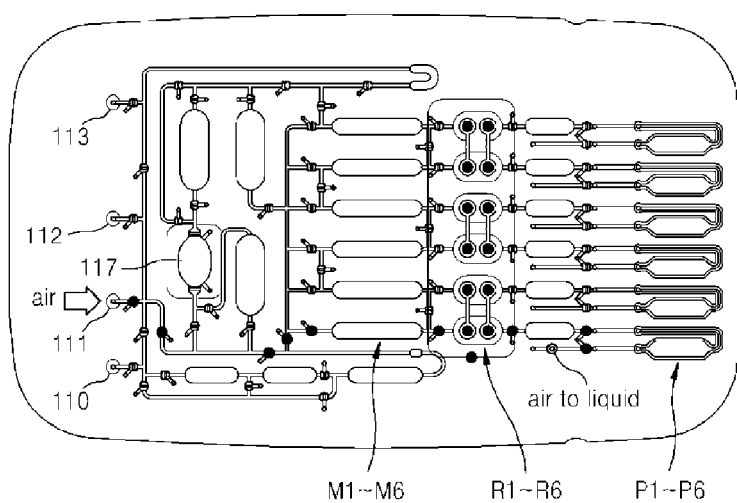
Figure 24T:
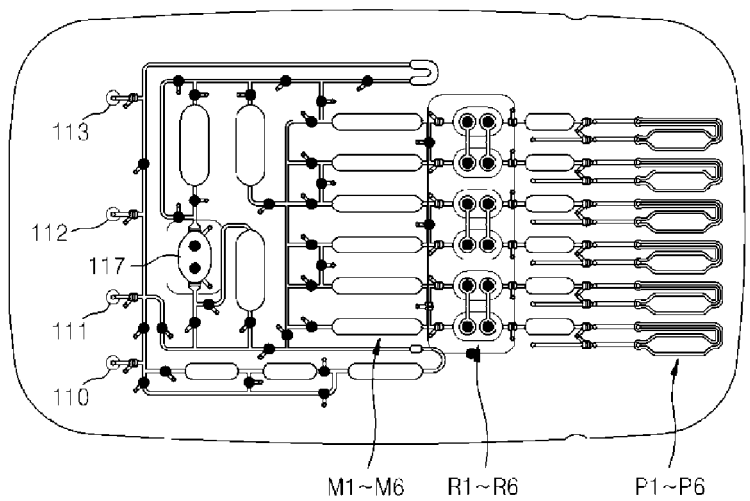

FIGS. 24A through 24T are plan views illustrating processes of performing operations according to the flowchart in FIG. 13 with valve operations required for the movement of a fluid in microfluidic system 1 according to an embodiment of the present invention.

The following exemplary processes illustrate using a microfluidic device described herein to capture cells from a sample, prepare a cell lysate containing nucleic acid (DNA), and determine the amount of DNA in the sample. As illustrated in FIG. 24A, opened valves in microfluidic system 1 are represented as black dots (●). The valves are opened to inject about 1 ml of a sample S including the examination sample into binding-lysis chamber 117 through inlet 112 by using external pressure. In this process, cells are bound by the plurality of particles disposed in binding-lysis chamber 117 and the resulting solution is released toward outlet 113 to the waste chamber of reagent supply device 50. When the solution flows out from a solution sensing portion, which is represented as a double circle (◎), and the change from liquid to air is detected at the solution sensing portion, the above process is stopped and a subsequent process is performed.

As illustrated in FIG. 24B, the indicated valves are opened to inject about 0.5 m of a washing buffer WB by using external pressure and the cells and the buffer are released toward outlet 113 to the waste chamber. When the solution flows out from the solution sensing portion and the change from liquid to air is detected at the solution sensing portion, the above process is stopped and a subsequent process is performed.

As illustrated in FIG. 24C, the indicatied valvesare opened to inject air through inlet 111 to dry the particles.

As illustrated in FIG. 24D, the indicatied valves in the parts represented as black dots (●) are opened to release a lysis buffer LB through inlet 110 to fill binding-lysis chamber 117. When the solution flows into the solution sensing portion and the change from air to liquid is detected, the above process is stopped and a subsequent process is performed.

As illustrated in FIG. 24E, the indicatied valves are opened to prepare paths to vent and a portion of membrane part 30 corresponding to the bottom surface of binding-lysis chamber 117 is then vibrated. Membrane part 30 is vibrated at a frequency of about 5 Hz to perform cell lysis by allowing particle beating in binding-lysis chamber 117 to be maintained for about 5 minutes.

As illustrated in FIG. 24F, the indicated valves are opened to fill each of the six metering chambers M1-M6 in an amount of about 4 μl. When the solution flows in to the solution sensing portion and the change from air to liquid is detected, the above process is stopped and a subsequent process is performed.

As illustrated in FIG. 24G, the indicated valves are opened to push the cell lysate in metering chamber M1 into rehydration chamber R1. When the solution flows out from a solution sensing portion and the change from liquid to air is detected at the solution sensing portion, the above process is stopped and a subsequent process is performed.

As illustrated in FIG. 24H, the indicatied valves are opened to push the cell lysate in metering chamber M2 into rehydration chamber R2. When the solution flows out from a solution sensing portion and the change from liquid to air is detected at the solution sensing portion, the above process is stopped and a subsequent process is performed.

As illustrated in FIG. 24I, the indicated valves are opened to push the cell lysate in metering chamber M3 into the rehydration chamber R3. When the solution flows out from a solution sensing portion and the change from liquid to air is detected at the solution sensing portion, the above process is stopped and a subsequent process is performed.

As illustrated in FIG. 24J, the indicated valves are opened to push the cell lysate in metering chamber M4 into rehydration chamber R4. When the solution flows out from a solution sensing portion and change from liquid to air is detected at the solution sensing portion, the above process is stopped and a subsequent process is performed.

As illustrated in FIG. 24K, the indicated valves are opened to push the cell lysate in metering chamber M5 into rehydration chamber R5. When the solution flows out from a solution sensing portion and the change from liquid to air is detected at the solution sensing portion, the above process is stopped and a subsequent process is performed.

As illustrated in FIG. 24L, the indicated valves are opened to push the cell lysate in metering chamber M6 into rehydration chamber R6. When the solution flows out from a solution sensing portion and the change from liquid to air is detected at the solution sensing portion, the above process is stopped and a subsequent process is performed.

As illustrated in FIG. 24M, the indicatied valves are opened and a portion of membrane part 30 forming the bottom surfaces of rehydration chambers R1-R6 is vibrated. Membrane part 30 may be vibrated at a frequency of about 0.2 Hz and in this process PCR reagents in rehydration chambers R1-R6 are dissolved and mixed with the cell lysate to form a PCR mixture.

As illustrated in FIG. 24N, the indicated valves are opened while air is injected into inlet 111 to push the PCR mixture into PCR chamber P1. When the fluid passing a solution sensing portion changes from air to liquid as detected by the solution sensing portion, the above process is stopped and a subsequent process is performed.

As illustrated in FIG. 24O, the indicated valves are opened to push the PCR mixture into PCR chamber P2. When the fluid passing a solution sensing portion changes from air to liquid as detected by the solution sensing portion, the above process is stopped and a subsequent process is performed.

As illustrated in FIG. 24P, the indicated valves are opened to push the PCR mixture into PCR chamber P3. When the fluid passing a solution sensing portion changes from air to liquid as detected by the solution sesing portion, the above process is stopped and a subsequent process is performed.

As illustrated in FIG. 24Q, the indicatied valves are opened to push the PCR mixture into PCR chamber P4. When the fluid passing a solution sensing portion is changed from air to liquid as detected by the solution sensing portion, the above process is stopped and a subsequent process is performed.

As illustrated in FIG. 24R, the indicatied valves are opened to push the PCR mixture into PCR chamber P5. When the fluid passing a solution sensing portion changes from air to liquid as detected by the solution sensing portion, the above process is stopped and a subsequent process is performed.

As illustrated in FIG. 24S, the indicatied valves are opened to push the PCR mixture into PCR chamber P6. When the fluid passing a solution sensing portion changes from air to liquid as detected by the solution sensing portion, the above process is stopped and a subsequent process is performed.

As illustrated in FIG. 24T, a PCR is performed in a state in which the indicated valves are opened and only valves disposed at front ends of the PCR chambers P1-P6 are closed.

Thus, a process in which a sample as an examination target is distributed into the plurality of PCR chambers from the reagent supply device to undergo a PCR, e.g., a series of operations, such as cell binding, lysis, and mixing with a PCR reagent, may be accurately and reproducibly performed in an integrated system by using the foregoing micro fluidic system 1.

One or more embodiments of the present inventive concept will now be described in detail with reference to the following examples. However, these examples are not intended to limit the scope of the one or more embodiments of the present inventive concept.

EXAMPLE 1

Manufacture of Lyophilized PCR Premix and Comparison of the Stabilities

A primer and a probe sequences used in a PCR of the example were mecA sequences of Table 1 to detect DNA of *Staphylococcus aureus*. Melting temperatures (Tm) of a forward primer, a reverse primer, and a probe below are 55° C., 51° C., and 46° C., respectively.

TABLE 1

| Oligo ID | Sequence | Label/Terminal location |
| --- | --- | --- |
| [3a]mecA-99 Forward primer | SEQ ID NO: 1 | No |
| [3a]mecA-99 Reverse primer | SEQ ID NO: 2 | No |
| [3a]mecA-99 Probe | SEQ ID NO: 3 | Cal610 |

In order to compare stabilities of control group 1 (PCR premix containing the components shown in Table 2), and experimental group 1 (PCR premix that are formed of components shown in Table 3), experiments were performed as follows:

The first and second reagents shown in Table 2 were prepared, and 2 ul of each of the reagents was injected into each of the first and the second wells in a PDMS reagent container. Then, the PDMS reagent container was placed in a lyophilizing apparatus (FTUT-6002, Operon) to prepare a lyophilized control group 1.

An experimental group 1 was prepared similar to the above. The first and second reagents shown in Table 3 were prepared, and 2 ul of each of the reagents was injected into each of the first and second wells in a PDMS reagent container. Then, the experimental group 1 was prepared after lyophilization.

Each of the control group 1 and experimental group 1 was placed in a 40° C. oven, and the reagent container from each of the control group 1 and experimental group 1 was taken out after 7 days, 14 days, 21 days, and 28 days. In each reagent container, a $10^3$ copy of target template of GeneBank EF190335.1 was added thereto, following a PCR, to then compare changes of the PCR values against the initial PCR values. The comparison of PCR values was performed by measuring mecA signal changes. The PCR proceeded with a denaturation at 95° C. for 1 second and an extension at 60° C. for 5 seconds, repeating for a total of 45 cycles.

Figure 8:
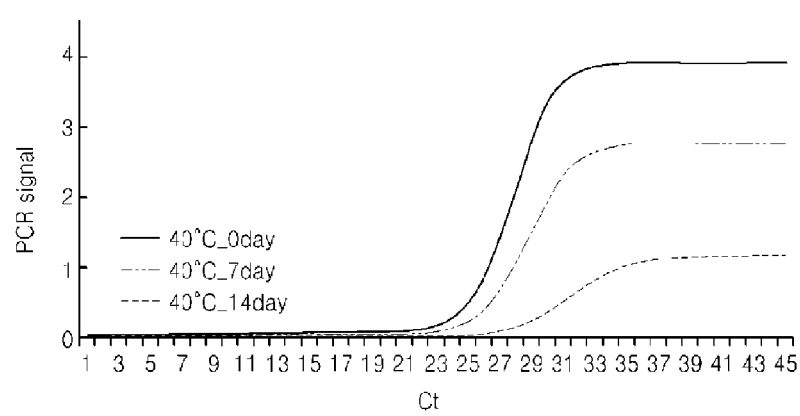
FIGS. 8 and 9 are graphical views of PCR signal plotted against threshold cycle (Ct) for PCR performed using reagents stored under specified conditions, which illustrate stabilities of the reagents.
Figure 9:
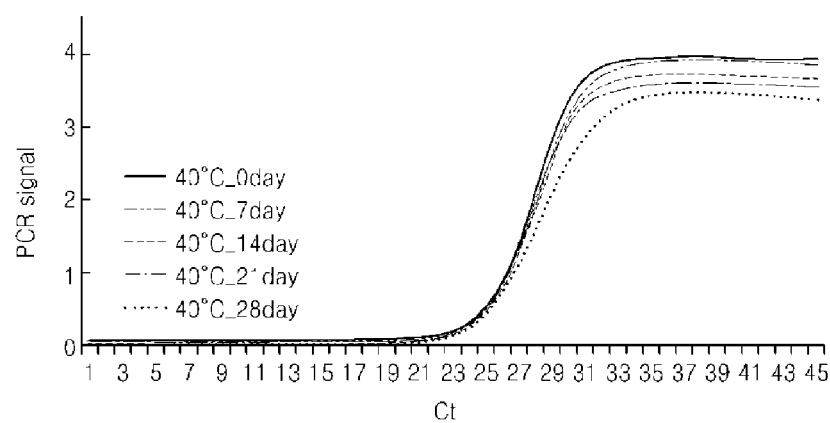

FIGS. 8 and 9 are graphical views illustrating stabilities of the control group 1 and the experimental group 1, respectively. In FIGS. 8 and 9, the X-axis represents a threshold cycle (Ct) value and the Y-axis represents a PCR signal. As shown in FIG. 8, the control group 1 has decreased a mecA signal, i.e., PCR signal, at 40° C. after 7 days. Also, it was confirmed that a threshold cycle (Ct) of the control group 1 increases in frequency by more than 5% of its initial value after maintaining the control group 1 for 14 days at 40° C. In addition, as shown in FIG. 9, it was confirmed that the experimental group 1 has maintained its initial value of its threshold cycle (Ct) until the 4th week at 40° C. Comparing the FIGS. 8 and 9, it was confirmed that the experimental group 1, unlike the control group 1, has a stable PCR signal even in the 4th week. Therefore, it is deemed that the experimental group 1 is a more stable PCR premix composition than the control group 1. In addition, in the control group 1, a primer and/or a probe of the second reagent were mixed to produce a gel type mixture, and the produced gel type mixture was solidified. Thus, the primer and/or probe were absorbed to the polymer such as PDMS composing the reagent container, resulting in the PCR premix with a low stability.

TABLE 2

| Component | Volume (ul) |
|---|---|
| The $1^{st}$ reagent | |
| dNTP | 16 |
| z-taq | 2 |
| Trehalose stabilizer | 10 |
| Antifoamer (SHA646, Saehan Chemical) 646(1%) | 10 |
| Triton-100(1%) | 5 |
| Water | 57 |
| The $2^{nd}$ reagent | |
| mecA primer/probe | 12 |
| 10X buffer (Takara PCR buffer) | 20 |
| Water | 68 |

TABLE 3

| Composition | Volume (ul) |
|---|---|
| The $1^{st}$ reagent | |
| dNTP | 16 |
| z-taq | 2 |
| Trehalose stabilizer | 10 |
| mecA primer/probe | 12 |
| Water | 60 |
| The $2^{nd}$ reagent | |
| 10X buffer (Takara PCR buffer) | 20 |
| Antifoamer (SHA646, Saehan Chemical) 646(1%) | 10 |
| Triton-100(1%) | 5 |
| Water | 65 |

EXAMPLE 2

Manufacture of Lyophilized PCR Premix and Comparison of the Stabilities

A primer and a probe sequences used in a PCR of the example were SA442 sequences of Table 4 to detect DNA of *Staphylococcus aureus*. Melting temperatures (Tm) of a forward primer, a reverse primer, and a probe below are 55° C., 51° C., and 46° C., respectively.

TABLE 4

| Oligo ID | Sequence (5'-3') | Label/Terminal location |
|---|---|---|
| SA442_76 Forward primer | CGTTGCATCGGAAACATTGT (SEQ ID NO: 4) | No |
| SA442_76 Reverse primer | ATGACCAGCTTCGGTACTACTAAAGAT (SEQ ID NO: 5) | No |
| SA442_76 Probe | FAM-TTCTGTATGTAAAAGCG-MGBNFQ (SEQ ID NO: 6) | FAM |

In order to compare stabilities of control group 2, i.e., PCR premix that are formed of components shown in Table 5, and experimental group 2, i.e., PCR premix that are formed of components shown in Table 6, experiments were performed as follows.

The first and second reagents shown in Table 5 were prepared, and 2 ul of each of the reagents was injected into each of the first and the second wells in a PDMS reagent container. Then, the PDMS reagent container was placed in a lyophilizing apparatus (FTUT-6002, Operon) to prepare a lyophilized control group 2.

An experimental group 2 was prepared similar to the above. The first and second reagents shown in Table 6 were prepared, and 2 ul of each of the reagents was injected into each of the first and second wells in a PDMS reagent container. Then, the experimental group 1 was prepared after lyophilization.

Each of the control group 2 and experimental group 2 was placed in a 40° C. oven, and the reagent container from each of the control group 2 and experimental group 2 was taken out after 7 days, 14 days, 21 days, and 28 days. In each reagent container, a $10^2$ of target template of GeneBank EF190335.1 was added thereto, following a PCR, to then compare changes of the PCR values against the initial PCR values. The comparison of PCR values was performed by measuring SA442 signal changes. The PCR proceeded with a denaturation at 95° C. for 1 second and an extension at 60° C. for 5 seconds, repeating for a total of 45 cycles.

Figure 25:
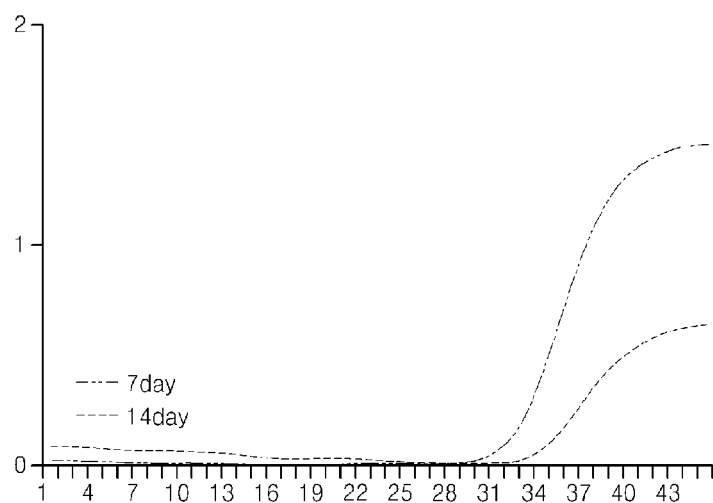
FIGS. 25 and 26 are graphical views illustrating stabilities of each of a control group 2 and an experimental group 2.
Figure 26:
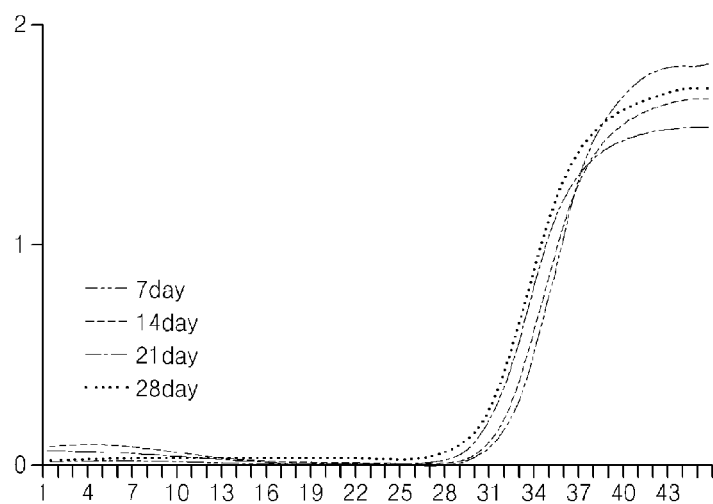

FIGS. 25 and 26 are graphical views illustrating stabilities of the control group 2 and the experimental group 2, respectively. In FIGS. 25 and 26, the X-axis represents a threshold cycle (Ct) value, and the Y-axis represents a PCR signal. As shown in FIG. 25, the control group 2 has a decreased SA442 signal, i.e., PCR signal, at 40 Ct after 7 days. Also, it was confirmed that a threshold cycle (Ct) of the control group 2 increases in frequency by more than 5% of its initial value after maintaining the control group 2 for 14 days at 40 Ct. In addition, as shown in FIG. 26, it was confirmed that the experimental group 2 has maintained its initial value of its threshold cycle (Ct) until the $4^{th}$ week at 40 Ct. Comparing the FIGS. 25 and 26, it was confirmed that the experimental group 2, unlike the control group 2, has a stable PCR signal even in the $4^{th}$ week. Therefore, it is deemed that the experimental group 2 is a more stable PCR premix composition than the control group 2. In addition, in the control group 2, a primer and/or a probe of the second reagent were mixed to produce a gel type mixture, and the produced gel type mixture was solidified. Thus, the primer and/or probe were absorbed to the polymer such as PDMS composing the reagent container, resulting in the PCR premix with a low stability.

TABLE 5

| Component | Volume (ul) |
|---|---|
| The $1^{st}$ reagent | |
| dNTP | 16 |
| z-taq | 2 |
| Trehalose stabilizer | 10 |
| Antifoamer (SHA646, Saehan Chemical) 646(1%) | 10 |
| Triton-100(1%) | 5 |
| Water | 57 |
| The $2^{nd}$ reagent | |
| SA442 primer/probe | 12 |
| 10X buffer (Takara PCR buffer) | 20 |
| Water | 68 |

TABLE 6

| Composition | Volume (ul) |
|---|---|
| The $1^{st}$ reagent | |
| dNTP | 16 |
| z-taq | 2 |
| Trehalose stabilizer | 10 |
| SA442 primer/probe | 12 |
| Water | 60 |
| The $2^{nd}$ reagent | |
| 10X buffer (Takara PCR buffer) | 20 |
| Antifoamer (SHA646, Saehan Chemical) 646(1%) | 10 |
| Triton-100(1%) | 5 |
| Water | 65 |

EXAMPLE 3

Performance Evaluation of PCR Premix Reagent Solidified within PDMS Reagent Container In order to confirm that PCR premix according to an embodiment of the present inventive concept has stability similar to a liquid PCR premix, an experiment was performed as follows. In more detail, a PCR initiated in the same way as Example 1. Herein, a control group 3 represents a liquid PCR premix, and the composition of the liquid PCR premix is shown in Table 7. An experimental group 3 represents a PCR premix in the PDMS reagent container, and the components of the PCR premix is the same as shown in Table 3.

TABLE 7

| Component | Volume (ul) |
|---|---|
| dNTP | 16 |
| z-taq | 2 |
| mecA primer/probe | 12 |
| 10X buffer (Takara PCR buffer) | 20 |
| Water | 68 |

The control group 3, i.e., the component of the liquid PCR premix was mixed in a PCR tube, and the mixture disposed via a pipette in 4 ul amounts into different PCR tubes. In each of the different PCR tubes, each 4 ul of a solution containing $10^4$, $10^3$, $10^2$, and $10^1$ copy of target nucleic acids was added thereto and stirred to initiate a PCR.

The experimental group 2 was mixed in the PDMS reagent container with 2 ul of each of the first and second reagents shown in Table 3, and each 4 ul of a solution containing $10^4$, $10^3$, $10^2$, and $10^1$ copy of target nucleic acids was added to 4 lyophilized reagents to then be melted and initiate a PCR reaction.

Figure 10:
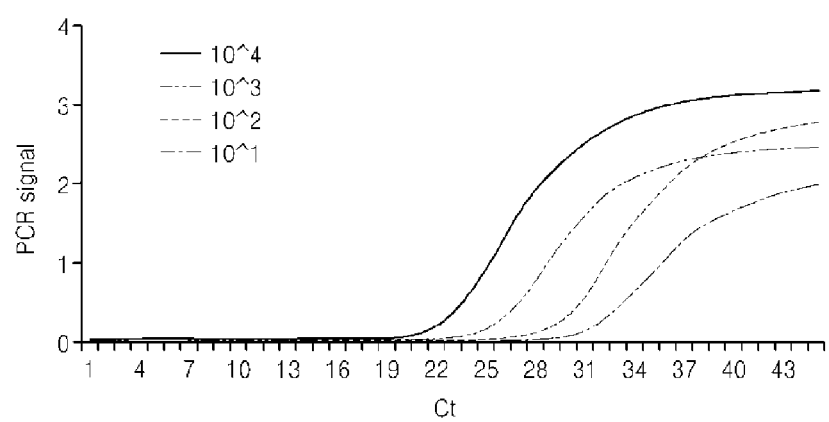
FIGS. 10 and 11 are graphical views of PCR signal plotted against threshold cycle (Ct) for PCR performed using reagents of specified concentrations, which illustrate performance of PCR of the reagents.
Figure 11:
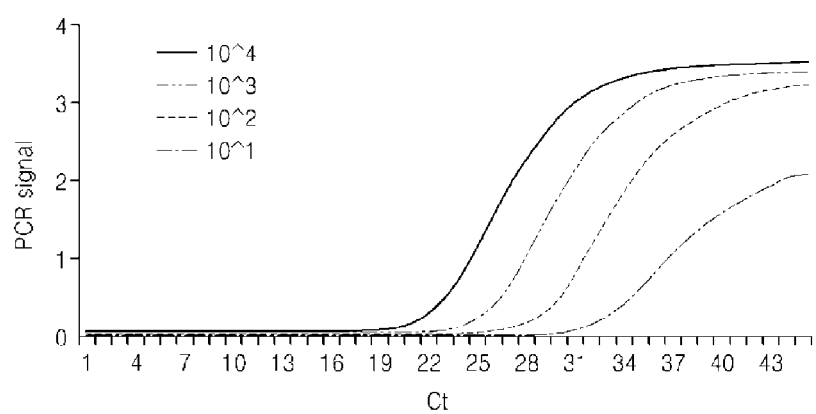

FIGS. 10 and 11 are graphical views illustrating performance of PCR dependent on the concentration of the target nucleic acids in the control group 3 and the experimental group 3. Threshold cycle (Ct) values depending on the concentration of the target nucleic acids as shown in FIGS. 10 and 11 are shown in Table 8. The Y-axis of the FIGS. 10 and 11 represents fluorescence intensity. As shown by a comparison of FIGS. 10 and 11, there is no difference in fluorescence intensity depending on which PCR occurs based on the two PCR premixes. That is, there is no difference in the performance of PCR between the two PCR premixes. Therefore, it was confirmed that the PCR premix in the reagent container according to an embodiment of the present inventive concept had a similar performance of PCR with the liquid PCR premix.

TABLE 8

| Concentration of the target nucleic acid | Ct value for Control group 2 | Ct value for Experimental group 2 |
|---|---|---|
| $10^4$ | 22.9 | 22.7 |
| $10^3$ | 26.3 | 26.1 |
| $10^2$ | 29.9 | 29.6 |
| $10^1$ | 32.0 | 32.9 |

According to an aspect of the present inventive concept, a reagent container may provide a reagent that may maintain its stability for a long period of time and its activity in a reaction of the reagent.

According to another aspect of the present inventive concept, a method of storing a reagent may maintain stability of the reagent for a long period of time and activity of the reagent in a reaction of the reagent.

According to another aspect of the present inventive concept, when a sample to be examined is injected into the microfluidic system for analyzing nucleic acid, a series of operations occurs in which cells contained in the sample are captured and nucleic acid is extracted from the captured cells, and the nucleic acid is then mixed with a nucleic acid amplification reagent to perform a nucleic acid amplification reaction that is sequentially performed in the system. Thus, easy and accurate examination may be possible. Because contamination from the outside, which may occur during a process after the extraction of nucleic acid from the sample to the nucleic acid amplification reaction, may be prevented, stable examination may be possible in comparison to the case in which each operation is performed in a separate system. Furthermore, since a multiplex PCR, in which a PCR is performed by dividing a single sample into a plurality of the same chambers, may be possible, the microfluidic system may be suitable for the purpose of various clinical diagnoses. It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A kit comprising:
   a reagent container comprising a first well and a second well, wherein
   the first well contains a first reagent comprising a nucleotide and a nucleic acid primer without a reaction buffer; and
   the second well contains a second reagent comprising a reaction buffer for amplifying a nucleic acid,
   wherein the container comprises a plurality of protrusions, and the first well and the second well are provided by two subgrooves separated from each other and recessed in a predetermined shape on the plurality of protrusions.

2. The kit of claim 1, wherein the first reagent comprises a deoxynucleotide triphosphate, a ribonucleotide triphosphate, or combination thereof; and, optionally, a probe nucleic acid.

3. The kit of claim 1, wherein the first reagent further comprises an enzyme or a stabilizer.

4. The kit of claim 1, wherein the first reagent is solidified.

5. The kit of claim 1, wherein the second reagent is solidified.

6. The kit of claim 1, wherein the first reagent is lyophilized.

7. The kit of claim 1, wherein the second reagent is lyophilized.

8. The kit of claim 1, wherein the reagent container further comprises a connection part that connects the first well and the second well to each other.

9. The kit of claim 8, wherein the connection part is a groove, a channel, a partition, or a film.

10. The kit of claim 1, wherein the first well comprises a first aperture, and the second well comprises a second aperture, wherein the aperture is provided by an open groove.

11. The kit of claim 10, wherein the reagent container is attached to a rehydration chamber, and the open groove of the first aperture and the open groove of the second aperture contact an outer surface of the rehydration chamber to form one channel.

12. A microfluidic system for analyzing nucleic acid, the microfluidic system comprising:

a rehydration chamber;
the kit of claim 1 attached to the rehydration chamber;
an amplification chamber; and
a flow channel system providing a fluid flow path between the rehydration chamber and the amplification chamber.

13. The microfluidic system of claim 12, wherein the rehydration chamber comprises two separated sub-chambers.

14. The microfluidic system of claim 13, wherein a side of the sub-chamber has a curved shape and a width of the sub-chamber is smallest at a center portion thereof.

15. The microfluidic system of claim 12, further comprising:
- a reagent supply device including a sample chamber in which a sample as an examination target is injected, one or more reagent chambers in which a reagent for extracting nucleic acid from the sample is injected, and a waste chamber in which the used reagent is discarded;
- a binding-lysis chamber in which cells are captured from the sample, the captured cells are lysed to form a cell lysate containing nucleic acid, and a plurality of particles for cell binding are disposed; and
- a flow channel system having an outlet and a plurality of inlets connected to the reagent supply device and forming an integrated fluid flow between the binding-lysis chamber, the rehydration chambers, and the amplification chambers.

16. A kit comprising:
a reagent container comprising a first well and a second well, wherein
the first well contains a first reagent comprising a nucleotide and a nucleic acid primer without a reaction buffer; and
the second well contains a second reagent comprising a reaction buffer for amplifying a nucleic acid,
wherein the container comprises a plurality of protrusions, and the first well and the second well are provided by two subgrooves separated from each other and recessed in a predetermined shape on the plurality of protrusions, wherein the wells have a curved shape comprising two curved side portions that meet at the center of the well, wherein the center of the well is narrower than the sides of the well.

17. A kit comprising:
a reagent container comprising a first well and a second well, wherein
the first well contains a first reagent comprising a nucleotide and a nucleic acid primer without a reaction buffer; and
the second well contains a second reagent comprising a reaction buffer for amplifying a nucleic acid,
wherein the container comprises a plurality of protrusions, and the first well and the second well are provided by two subgrooves separated from each other and recessed in a predetermined shape on the plurality of protrusions, wherein an external angle $\theta$ formed by corners of both sides of the first well and the second well at a position having the narrowest width is in a range of about 30 degrees to about 90 degrees.

18. A method of storing a reagent, the method comprising:
disposing a first reagent comprising a nucleotide and nucleic acid primer into a first well of a reagent container of claim 1, wherein the first well of the reagent container does not contain a reaction buffer;
disposing a second reagent comprising a reaction buffer into the second well of the reagent container; and
solidifying the first reagent by drying;
wherein the first and the second reagent are for amplifying nucleic acids.

19. The method of claim 18, wherein the first reagent further comprises an enzyme.

* * * * *